United States Patent
Periana et al.

(10) Patent No.: US 11,396,492 B2
(45) Date of Patent: Jul. 26, 2022

(54) DIRECT OXIDATIVE AMINATION OF HYDROCARBONS

(71) Applicants: University of Florida Research Foundation, Incorporated, Gainesville, FL (US); Hyconix, Inc., Chicago, IL (US)

(72) Inventors: Roy A. Periana, Jupiter, FL (US); Brian G. Hashiguchi, Naperville, IL (US); Sae Hume Park, Jupiter, FL (US); Niles Jensen Gunsalus, Palm City, FL (US)

(73) Assignees: University of Florida Research Foundation, Incorporated, Gainesville, FL (US); Hyconix, Inc., Chicago, IL (US)

(*) Notice: Subject to any disclaimer, the term of this patent is extended or adjusted under 35 U.S.C. 154(b) by 0 days.

(21) Appl. No.: 16/767,831

(22) PCT Filed: Nov. 30, 2018

(86) PCT No.: PCT/US2018/063489
§ 371 (c)(1),
(2) Date: May 28, 2020

(87) PCT Pub. No.: WO2019/109045
PCT Pub. Date: Jun. 6, 2019

(65) Prior Publication Data
US 2020/0377448 A1 Dec. 3, 2020

Related U.S. Application Data

(60) Provisional application No. 62/593,320, filed on Dec. 1, 2017.

(51) Int. Cl.
C07C 303/40 (2006.01)
C07C 209/62 (2006.01)
(Continued)

(52) U.S. Cl.
CPC .......... *C07C 303/40* (2013.01); *C07B 43/00* (2013.01); *C07B 43/04* (2013.01); *C07B 43/06* (2013.01); *C07C 209/62* (2013.01)

(58) Field of Classification Search
None
See application file for complete search history.

(56) References Cited

U.S. PATENT DOCUMENTS

| 4,113,756 A * | 9/1978 | Johnson | C01G 15/00 423/111 |
|---|---|---|---|
| 9,394,247 B2 | 7/2016 | Besson et al. | |
| 2017/0275222 A1 | 9/2017 | Periana et al. | |

FOREIGN PATENT DOCUMENTS

| CN | 102408285 A | 4/2012 |
|---|---|---|
| RU | 2015105774 A | 9/2016 |
| WO | WO 2012/160112 A1 | 11/2012 |

OTHER PUBLICATIONS

Ochiai ("Highly Regioselective Amination of Unactivated Alkanes by Hypervalent Sulfonylimino-3-Bromane" Science, 2011, 332, p. 448-451) (Year: 2011).*

(Continued)

*Primary Examiner* — Amy C Bonaparte
(74) *Attorney, Agent, or Firm* — Leydig, Voit & Mayer, Ltd.

(57) ABSTRACT

Provided is a process for converting a hydrocarbon comprising at least one C—H bond to a nitrogen-functionalized product. The process comprises contacting a hydrocarbon and (i) an oxidizing electrophile comprising (a) a main group element or transition metal in oxidized form and (b) at least one nitrogen-containing ligand, or (ii) an oxidant and a reduced form of an oxidizing electrophile comprising (a) a main group element or transition metal and (b) at least one nitrogen-containing ligand, in a solvent to provide the nitrogen-functionalized product and an electrophile reduction (Continued)

product. Further provided is an oxidizing composition comprising the oxidizing electrophile with at least one nitrogen-containing ligand and a non-oxidizable liquid.

14 Claims, 9 Drawing Sheets

(51) Int. Cl.
  *C07B 43/06*   (2006.01)
  *C07B 43/00*   (2006.01)
  *C07B 43/04*   (2006.01)

(56) References Cited

OTHER PUBLICATIONS

Hasiguchi ("Main-Group Compounds Selectively Oxidize Mixtures of Methane, Ethane, and Propane to Alcohol Esters" Science, 2014, 343, p. 1232-1237) (Year: 2014).*
Stavropoulos ("Metal-Catalyzed and Metal-Free Intermolecular Amination of Light Alkanes and Benzenes" Comments Mod Chem A Comments Inorg Chem. 2017, 37, p. 1-57) (Year: 2017).*
Rat ("C—H Bond Activation Mediated by Inorganic and Organometallic Compounds of Main Group Metals" Advances in Organometallic Chemistry, 70, 2018, p. 233-311) (Year: 2018).*
Trenner ("Direct Oxidative Allylic and Vinylic Amination of Alkenes through Selenium Catalysis" Angew. Chem. Int. Ed. 52, 2013, p. 8952-8956; including Supporting Information (SI) p. S1-S56) (Year: 2013).*
Greene ("Benzenesulfonamide" Greene's Protective Groups in Organic Synthesis, 2007, p. 855-859) (Year: 2007).*
Wikipedia definition for ligand: https://en.wikipedia.org/wiki/Ligand, downloaded on Jul. 19, 2021 (Year: 2021).*
Gomez Aranda ("The Addition of Aromatic Amines to Alkenes in the Presence of Thallium(III)acetate", Synthesis, 1974, p. 504-505) (Year: 1974).*
Sun ("Peroxodisulfate-mediated selenoamination of alkenes yielding amidoselenide-containing sulfamide and azoles" Chem. Commun. 2016, 52, p. 8471-8474) (Year: 2016).*
Uddin ("Amination of alkenes via thallium complexes", Journal of the Bangladesh Chemical Society, 1992, vol. 5, p. 23-27) (Year: 1992).*
Ciminale ("Oxidative Activation in Aromatic Substitutions. Reactions of N,N-dimethylanilines with Secondary Anilines Promoted by Thallium Triacetate" J. Org. Chem. 1999, 64, p. 2459-2464) (Year: 1999).*
Weinreb ("Bis[N-(p-toluenesulfonyl)]selenodiimide" e-EROS, 2001, p. 1-2, downloaded from http://www3.interscience.wiley.com/cgi-bin/mrwhome/104554785/HOME) (Year: 2001).*
Hu ("Aminotellurinylation of Olefins with Benzenetellurinyl Acetate and Ethyl Carbamate" Chemistry Letters, 1987, p. 1327-1330) (Year: 1987).*
Huang ("An Acid-Catalyzed Formal Allylic C—H Oxidation of Aryl Cycloalkenes with N-Propylthiosuccinimide" Organic Letters, 2011, 13, p. 1548-1551) (Year: 2011).*
Alberti ("Homolytic substitution in indolinone nitroxides. IV. Reactions with aminyl radicals. A spectroscopic and crystallographic study", Tetrahedron, 1987, 43, p. 3031-3040) (Year: 1987).*
Bagchi et al., "A Versatile Tripodal Cu(I) Reagent for C—N Bond Construction via Nitrene-Transfer Chemistry: Catalytic Perspectives and Mechanistic Insights on C—H Aminations/Amidinations and Olefin Aziridinations," *J. Am. Chem. Soc.*, 136(32): 11362-11381 (Aug. 5, 2014).
Boursalian et al., "Pd-Catalyzed Aryl C—H Imidation with Arene as the Limiting Reagent," *J. Am. Chem. Soc.*, 135(36): 13278-13281 (Sep. 3, 2013).
Iglesias et al., "Palladium-Catalyzed Intermolecular C(sp$^3$)-H Amidation," *Agnew. Chem. Int. Ed.*, 51(9): 2225-2228 (Feb. 27, 2012).
Kubler et al., "Ferrocenyl-phosphonium ionic liquids—synthesis, characterisation and electrochemistry," *Dalton Trans.*, 43(9): 3750-3766 (Jan. 1, 2014).
Park et al., "Transition Metal-Catalyzed C—H Amination: Scope, Mechanism, and Applications," *Chem. Rev.*, 117(13): 9247-9301 (Jul. 12, 2017).
Wang et al., "Copper-Catalyzed Oxidative Dehydrogenative C(sp$^3$)-H Bond Amination of (Cyclo)Alkanes using NH-Heterocycles as Amine Sources," *ChemSusChem*, 10(15): 3075-3082 (Aug. 10, 2017).
Zhang et al., "Direct methylation and trifluoroethylation of imidazole and pyridine derivatives," *Chemical Common.*, 18: 2334 (Jan. 1, 2003).
European Patent Office, International Search Report and the Written Opinion in International Application No. PCT/US2018/063489 (dated Mar. 15, 2019).

* cited by examiner

DIRECT OXIDATIVE AMINATION OF HYDROCARBONS

CROSS-REFERENCE TO RELATED APPLICATIONS

This patent application is a U.S. national phase of International Patent Application No. PCT/US2018/063489, filed Nov. 30, 2018, which claims the benefit of U.S. Provisional Patent Application 62/593,320, filed Dec. 1, 2017, the disclosure of which is incorporated herein by reference in its entirety for all purposes.

BACKGROUND OF THE INVENTION

Low molecular weight alkyl and aryl amines (e.g., $C_1$-, $C_2$-, $C_3$- and $C_6$-based carbon fragments) are among the largest volume amines utilized in the chemical industry. These materials are important to a broad range of chemical industries, including, for example, rubber, dyes, pharmaceuticals, polymeric resins, and fibers. However, efficient and low-cost techniques for using relatively unreactive small molecules, such as alkanes, to produce low molecular weight alkyl and aryl amines are currently underdeveloped in the chemical industry. These small molecule feedstocks are highly abundant and readily accessible, yet, underutilized due to a variety of drawbacks. For example, during the conversion of methane to methylamine, the homolytic C—H bond strength of the starting material, methane, is ~105 kcal/mol. In comparison, the homolytic C—N and C—H bond strengths of the product, methylamine, are ~87 kcal/mol and ~92 kcal/mol, respectively. Thus, it is common for the product (i.e., C—N or C—H bonds) of the oxidation process to be more reactive than the starting material in free radical reactions. The most common oxidation reactions are based on free radical reaction mechanisms. Consequently, this unfavorable reactivity to free radicals results in low selectivity to products and the formation of by-products produced by over-oxidation of the products.

Common techniques for the formation of C—N bonds either require harsh conditions resulting in low product selectivity, including by-products formed by over-oxidation, or substrates that are highly unique and expensive due to their complexity. Conventionally, alkyl and aryl amines have been prepared from reactive intermediates such as olefins or alcohols, and/or using expensive reagents such as nitric acid or chlorine gas (see, for example, FIG. 1). Typically, these routes are energy intensive, expensive, and generate excessive emissions and waste. To date, the only methods that have been reported for the direct, one-step, conversion of light alkanes, such as methane, ethane, or propane, with $NH_3$ directly to the corresponding amine (e.g., methylamine, ethylamine, etc.) utilize photochemical reactions. However, photochemical reactions are expensive and suffer from selectivity issues and over-oxidation.

Common alternatives utilized to form C—N bonds from C—H bonds include mechanisms that proceed through a metal nitrenoid, free nitrenoid, nitrogen radical, and/or organo-nitrenoid. However, these techniques have drawbacks, such as reactive intermediates (e.g., radical or nitrene intermediates), may necessitate expensive catalysts or reagents, and often require high molecular weight substrates, intramolecular reactivity, and/or directing groups.

To our knowledge, the only examples of C—H to C—N conversion that operate by C—H activation, a process that does not utilize a radical or nitrene intermediate, require an intramolecular process and/or a heteroatom directing group within the substrate. Thus, non-radical, non-nitrene based alternatives to convert C—H bonds of unfunctionalized low molecular weight alkanes and arenes directly to the amine are not known.

Accordingly, there remains a need to provide techniques for the oxidation of relatively unreactive small molecules to directly afford their amine counterparts. Particularly useful methods will be mild and cost efficient to convert readily available small molecule feedstocks into useful amine-based products and chemical building blocks.

BRIEF SUMMARY OF THE INVENTION

The invention provides a process for converting a hydrocarbon comprising at least one C—H bond to a nitrogen-functionalized product, comprising, consisting essentially of, or consisting of: contacting the hydrocarbon and either (i) an oxidizing electrophile comprising (a) a main group element or transition metal in oxidized form and (b) at least one nitrogen-containing ligand, or (ii) an oxidant and a reduced form of an oxidizing electrophile comprising (a) a main group element or transition metal and (b) at least one nitrogen-containing ligand, in a solvent to provide the nitrogen-functionalized product and an electrophile reduction product; and optionally separating the nitrogen-functionalized product and the electrophile reduction product.

The invention also provides an oxidizing composition comprising, consisting essentially of, or consisting of: (a) an oxidizing electrophile comprising a main group element or transition metal in oxidized form and at least one nitrogen-containing ligand; (b) a non-oxidizable liquid selected from the group consisting of a fluorinated hydrocarbon, a sulfone, a deactivated arene, a deactivated aliphatic, a deactivated heteroarene, a deactivated heteroaliphatic, a compound of the formula $HNY_2$ or $H_2NY$, and a combination thereof, wherein Y is an electron-withdrawing group; and (c) optionally one or more additives of the formula $Z_a(NH_nY_{2-n})_p$, wherein Z is a cation, Y is an electron-withdrawing group. Y groups can include aryl (e.g., deactivated aryl), —F, —COR, —C(O)OR, —C(O)NRR', —$NO_2$, —NO, —$CH_2SO_2$, —$SO_2R$, —$SO_2F$, —$SO_2OH$, —$SO_2NH_2$, or —P(O)RR', in which R and R' are the same or different and each is aliphatic, heteroaliphatic, aromatic, or heteroaromatic, a is 1 to 5, n is 0 or 1, and p is 1 to 5.

DETAILED DESCRIPTION OF THE INVENTION

The invention provides a process for converting a hydrocarbon comprising at least one C—H bond to a nitrogen-functionalized product, comprising, consisting essentially of, or consisting of: contacting the hydrocarbon and either (i) an oxidizing electrophile comprising (a) a main group element or transition metal in oxidized form and (b) at least one nitrogen-containing ligand, or (ii) an oxidant and a reduced form of an oxidizing electrophile comprising (a) a main group element or transition metal and (b) at least one nitrogen-containing ligand, in a liquid medium comprising a solvent (e.g., a non-oxidizable liquid, such as a fluorinated hydrocarbon, a sulfone, a deactivated arene, a deactivated aliphatic, a deactivated heteroarene, a deactivated heteroaliphatic, a compound of the formula HNY$_2$ or H$_2$NY, or a combination thereof) to provide the nitrogen-functionalized product and an electrophile reduction product; and optionally separating the nitrogen-functionalized product and the electrophile reduction product.

The process converts a hydrocarbon comprising at least one C—H bond to a nitrogen-functionalized product. The effectiveness of the process, described herein, is best viewed in terms of the oxidizing electrophile's ability to react with a relatively inert C—H bond of a functionalized or unfunctionalized hydrocarbon to form a nitrogen-functionalized product. Hydrocarbons typically require harsh reaction conditions (e.g., free radical-based chemistry) to undergo chemical transformations, and traditional techniques typically result in complex product mixtures. In contrast to conventional techniques, the process, described herein, does not require harsh reaction conditions to form the N-functionalized product and subsequent amine. More particularly, the process does not form the N-functionalized product and subsequent amine by a free radical mechanism. Without wishing to be bound by any theory, it is believed that the mechanism by which the process converts a hydrocarbon comprising at least one C—H bond to a nitrogen-functionalized product occurs through an electrophilic C—H activation ("CHA") reaction.

Figure 1:
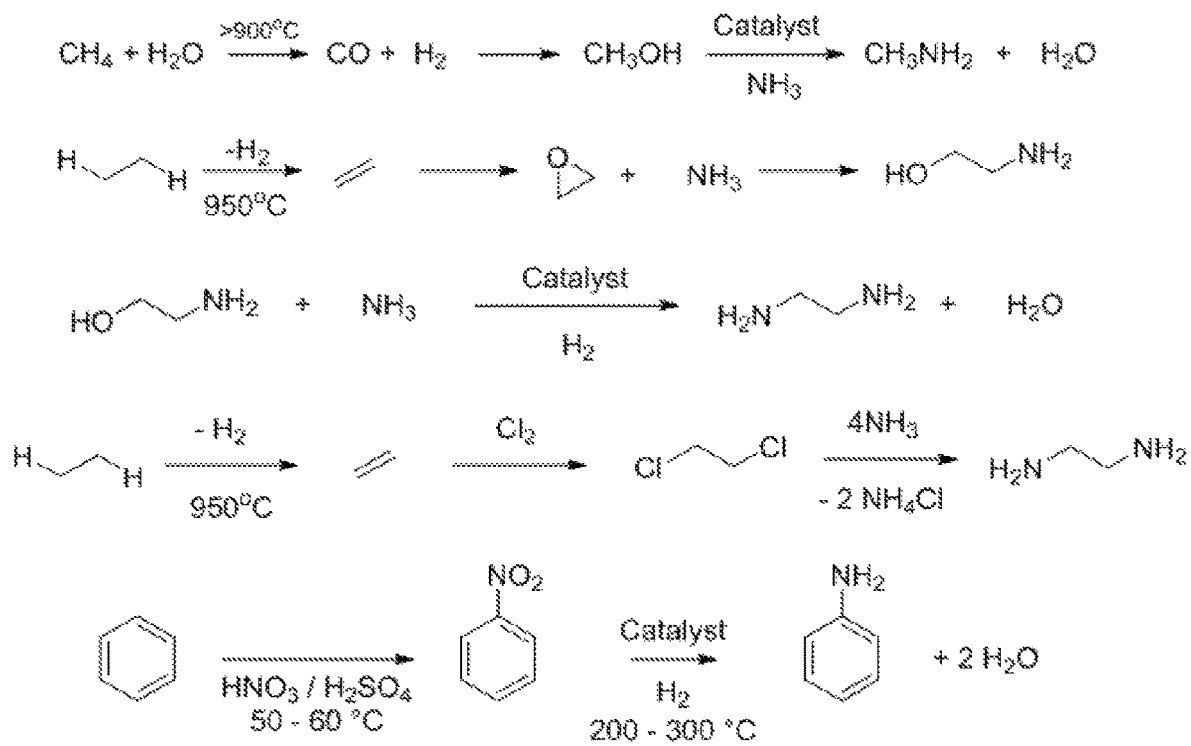
FIG. 1 illustrates current industrial routes to produce commercial volumes of organic amines.
Figure 2:
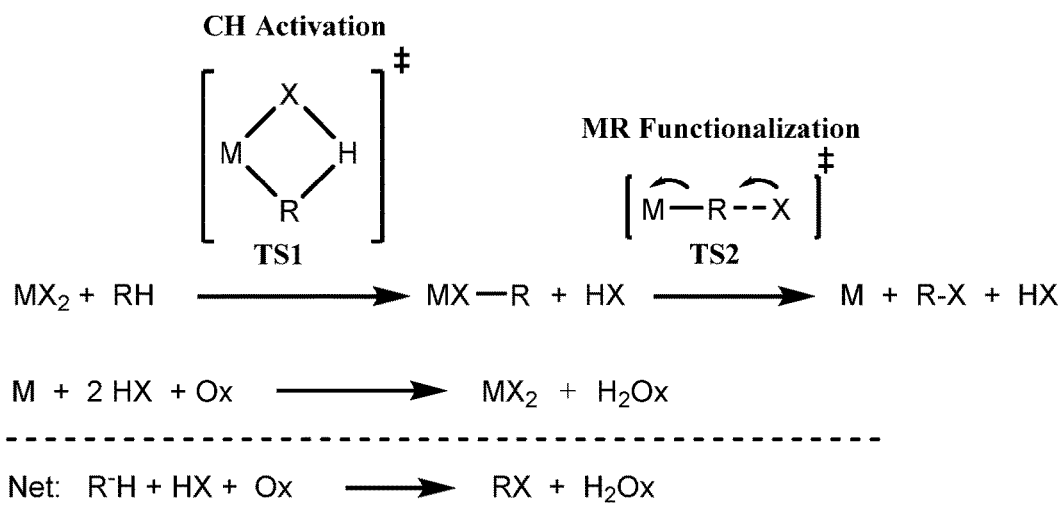
FIG. 2 illustrates the conversion of R—H to R—X via C—H activation and M-R functionalization.

An important emerging approach to the direct oxidation of C—H bonds of alkanes to C—X bonds (where X is a heteroatom) is based on the electrophilic C—H activation reaction shown in FIG. 2. This reaction involves the species MX$_2$, which reacts directly with R—H (i.e., C—H bond of an alkane) to generate H—X and MX—R intermediates. A key advantage of the C—H activation reaction is that cleavage of the R—H bond proceeds by a concerted process involving a single transition state, TS1, whereas the R—H bond is cleaved the new M-R and H—X bonds are simultaneously created. Three important advantages of this concerted cleavage are (i) no reactive species (e.g., free radicals, carbocations or carbanions) are generated that can lead to unselective reactions, (ii) as the energy input required to cleave the R—H bond is moderated by the energy released in the formation of the new M-R and H—X bonds, these reactions can be quite facile, and (iii) the properties of M and X can be adjusted to ensure that the product, R—X, is less reactive than the substrate, R—H. Using MX$_2$ species that can subsequently undergo redox reactions allows the C—H activation to be coupled to an M-R functionalization reaction. The resulting M-R functionalization reaction proceeds by a concerted process involving a single transition state, TS2, and can selectively generate functionalized products, R—X, and reduced species, M. As shown in FIG. 2, reoxidation of M with an oxidant (Ox) can allow an overall reaction of R—H with Ox to generate R—X without consumption of MX$_2$.

Previously, it has been shown that an electrophilic oxidant of the formula M(OY)$_2$ is capable of facilitating the direct oxidation of an alkane to form the corresponding alcohol and/or diol, via an electrophilic C—H activation ("CHA") reaction. It is particularly effective when carried out in the corresponding acid solvent, HOY (e.g., H$_2$SO$_4$, HSO$_3$CF$_3$, HCO$_2$CF$_3$, and HSO$_3$CH$_3$). However, there is no precedent for such CHA reaction with an electrophilic oxidant of the formula M(NY$_2$)$_2$ to form the corresponding amine and/or diamine. Due to the increased basicity of nitrogen, relative to oxygen, it would be expected that nitrogen forms a stronger bond to the metal center ("M"), thereby increasing the electron density around the metal center and reducing its electrophilicity. In addition, for a CHA reaction to occur, loss of a ligand, such as NY$_2$, must occur first. Due to the increased basicity of nitrogen and increased electronegativity of oxygen, the loss of NY$_2$ would not be expected to happen as readily as the loss of OY. Thus, it would not be obvious that the process of direct oxidation of an alkane to form the corresponding alcohol, via an electrophilic CHA reaction, could be extended to form a corresponding amine.

The process comprises converting a hydrocarbon comprising at least one C—H bond to a nitrogen-functionalized product. Any hydrocarbon is suitable, provided that it has at least one C—H bond (e.g., 1, 2, 3, 4, 5, 6, 7, 8, 9, 10, etc. C—H bonds). For example, the hydrocarbon can be substituted, unsubstituted, full or partially saturated, unsaturated, branched, straight-chained, cyclic, aromatic, or a combination thereof. Accordingly, the hydrocarbon can be selected from alkane, alkene, alkyne, cycloalkane, cycloalkene, heterocycloalkane, heterocycloalkene, arene, and heteroarene, each of which is optionally substituted. Typically, the hydrocarbon comprises from 1 to 20 (i.e., 1, 2, 3, 4, 5, 6, 7, 8, 9, 10, 11, 12, 13, 14, 15, 16, 17, 18, 19, or 20) carbons and preferably comprises from 1 to 10, 1 to 8, or 1 to 6 carbons. Non-carbon heteroatoms can also be present in the hydrocarbon, as described herein.

In some embodiments, the core structure of the hydrocarbon does not comprise a heteroatom. In such embodiments, the hydrocarbon can be selected from alkane, alkene, alkyne, cycloalkane, cycloalkene, and arene. In some instances, the hydrocarbon is alkane, alkene, or arene. The term "alkane" implies a straight-chain or branched alkane containing from, for example, from about 1 to about 8 carbon atoms, e.g., from about 1 to about 6 carbon atoms. The terms "alkene" and "alkyne," as used herein, mean a linear alkane that contains at least one C—C double bond or C—C triple bond, respectively, and contains from, for example, about 2 to about 8 carbon atoms (branched groups are about 3 to about 8 carbons atoms), e.g., from about 3 to about 6 carbon atoms (branched groups are about 3 to about 6 carbons atoms). The term "cycloalkane," as used herein, means a cyclic alkane moiety containing from, for example, 3 to 6 carbon atoms or from 5 to 6 carbon atoms. The term "cycloalkene" refers to a cycloalkane, as described herein, with at least one C—C double bond in the ring. The term "arene" refers to an unsubstituted or substituted aromatic carbocyclic moiety that is planar and comprise 4n+2 π electrons, according to Hückel's Rule, wherein n=1, 2, or 3, as commonly understood in the art. The term "arene" includes monocyclic and polycyclic aromatics and generally contains from, for example, 6 to 30 carbon atoms (e.g., from 6 to 18 carbons, from 6 to 14 carbons, or from 6 to 10 carbons).

An exemplary list of hydrocarbons that do not comprise a heteroatom includes, but is not limited to, methane, ethane, ethylene, ethyne, propane, propylene, propyne, butane, butene, isobutane, isobutene, pentane, pentene, isopentane, isopentene, isoprene, 2,3-dimethylbutane, cyclopentane, cyclohexane, cyclohexene, benzene, toluene, hexane, heptane, octane, nonane, decane, naphthalene, and anthracene. In certain embodiments, the hydrocarbon is methane, ethane, ethylene, propane, propylene, benzene, or a combination thereof.

In some embodiments, the hydrocarbon substrate comprises a heteroatom, such as at least one N, O, S, or P atom. In such embodiments, the hydrocarbon can be selected from heteroalkane, heteroalkene, heteroalkyne, heterocycloalkane, heterocycloalkene, and heteroarene, in which the terms "alkane," "alkene," "alkyne," "cycloalkane," "cycloalkane," and "arene" are as described herein. Examples of a hydrocarbon that comprises a heteroatom include an amine, imine, nitrile, alcohol, ether, aldehyde, ketone, acid, ester, thiol, thioether, or a combination thereof.

In some embodiments, the process comprises contacting the hydrocarbon with an oxidizing electrophile comprising (a) a main group element or transition metal in oxidized form and (b) at least one nitrogen-containing ligand in a solvent to provide the nitrogen-functionalized product and an electrophile reduction product; and optionally separating the nitrogen-functionalized product and the electrophile reduction product. The main group element or transition metal in oxidized form can be any suitable main group element or transition metal in any suitable oxidation state. For example, the main group element can have an oxidation state of +8, +7, +6, +5, +4, +3, +2, or +1, particularly an oxidation state of +6, +5, +4, +3, or +2. In preferred embodiments, the main group element or transition metal in oxidized form has any oxidation state suitable for a two-electron reduction/oxidation process. While the reactions can be run in air (e.g., in the presence of oxygen) or an inert atmosphere, the nature of the contacting step is such that the oxidizing electrophile can oxidize the hydrocarbon without the need for molecular oxygen as a reactant.

The oxidizing electrophile can be prepared using any suitable method. For example, the oxidizing electrophile can be prepared separately as a stable and isolable compound or the oxidizing electrophile can be generated in situ from a reduced form of the oxidizing electrophile, generated in situ through a substitution reaction, or generated in situ through a dehydration reaction. A combination of any of these methods can also be used.

In some embodiments, the process comprises contacting the hydrocarbon with an oxidant and a reduced form of an oxidizing electrophile comprising (a) a main group element or transition metal and (b) at least one nitrogen-containing ligand in a solvent to provide the nitrogen-functionalized product and an electrophile reduction product; and optionally separating the nitrogen-functionalized product and the electrophile reduction product. As used herein, "a reduced form of the oxidizing electrophile" refers to any reduced form of an oxidizing electrophile comprising a main group element or transition metal. Generally, the reduced form of the oxidizing electrophile comprises main group element or transition metal with a two-electron difference in oxidation state, relative to the oxidizing electrophile comprising a main group element or transition metal. For example, the reduced form of the oxidizing electrophile will have a main group element or transition metal in an oxidation state of +6, +5, +4, +3, +2, or +1 or a neutral oxidation state. In certain embodiments, the reduced form of the oxidizing electrophile comprises the main group element or transition metal in an oxidation state of +4, +3, +2, or +1 or a neutral oxidation state. In some embodiments, the reduced form of the oxidizing electrophile is any suitable chemical variant of the oxidizing electrophile, such that the main group element or transition metal has been reduced by two electrons.

In embodiments where the process comprises an oxidant and a reduced form of an oxidizing electrophile, the oxidant can be any suitable oxidant capable of generating the main group element or transition metal in oxidized form. For example, the oxidant can be molecular oxygen, a peroxide, nitric oxide, nitrous oxide, nitric acid, sulfur trioxide, ozone, hydrazine or a combination thereof. The peroxide can be, e.g., an organic peroxide, inorganic peroxide, hydrogen peroxide, or a combination thereof. In some embodiments, the oxidant can be an organic oxidant. For example, the oxidant can be a quinone, organohydrazine, methoxyamine, hydroxylamine, or a nitroxide. In certain embodiments, the oxidant is molecular oxygen, ozone, hydrogen peroxide, organoperoxide, nitric acid, hydrazine, organohydrazine, methoxyamine, hydroxylamine, or a combination thereof.

The oxidizing electrophile or reduced form of the oxidizing electrophile can comprise any suitable main group element or transition metal. For example, the oxidizing electrophile can comprise cobalt, rhodium, iridium, nickel, palladium, platinum, copper, silver, gold, zinc, cadmium, mercury, aluminum, gallium, indium, thallium, germanium, tin, lead, arsenic, antimony, bismuth, selenium, tellurium, polonium, iodine, or astatine. In some instances, the oxidizing electrophile comprises the element mercury, thallium, lead, antimony, selenium, tellurium, bismuth, iodine, gold, platinum, palladium, silver, iridium, rhodium, osmium, or rhenium. In embodiments in which the oxidizing electrophile comprises iodine, the iodine can be present as any suitable form that is reduced, oxidized, or neutral. For example the iodine can be present in neutral form such as $I_2$; the iodine can be present in a reduced form such as an aromatic iodide; the iodine can be present in an oxidized form, such as $^F$PhI(NTf$_2$)$_2$.

In certain embodiments, the oxidizing electrophile or reduced form of the oxidizing electrophile comprises a main group element. The main group element typically includes elements in the post-transition metal and non-metal groups of the periodic table and include, for example, elements with atomic numbers 33, 34, 35, 49, 50, 51, 52, 53, 81, 82, and 83 (i.e., arsenic, selenium, bromine, indium, tin, antimony, tellurium, iodine, thallium, lead, and bismuth). In an embodiment, the term "main group element" refers to any element having filled 4d or 5d orbitals, which undergoes a net two-electron change in oxidation state. In some instances, the main group elements include thallium, indium, lead, antimony, tin, selenium, tellurium, iodine, arsenic, and bismuth. In certain embodiments, the main group element is antimony, tellurium, bismuth, or arsenic. In other embodiments, the oxidizing electrophile comprises Sb(V), Te(VI), Te(IV), Bi(V), Se(VI), Se(IV), As(V), I(V), I(III), or Sn(IV).

In certain embodiments, the oxidizing electrophile or reduced form of the oxidizing electrophile comprises a transition metal. The transition metal typically includes "late" transition metal elements of the periodic table, for example, elements with atomic numbers 26, 27, 28, 29, 30, 44, 45, 46, 47, 48, 76, 77, 78, 79, and 80 (i.e., iron, cobalt, nickel, copper, zinc, ruthenium, rhodium, palladium, silver, cadmium, osmium, iridium, platinum, gold, and mercury). In an embodiment, the term "transition metal" refers to any element in groups 3-12 of the periodic table, which undergoes a net two-electron change in oxidation state. In some instances, the transition metal is manganese, technetium, rhenium, iron, ruthenium, osmium, cobalt, rhodium, iridium, nickel, palladium, platinum, copper, silver, gold, zinc, cadmium, or mercury. In certain embodiments, the transition metal is mercury, gold, platinum, palladium, silver, iridium, rhodium, osmium, or rhenium.

In some embodiments, the oxidizing electrophile is present in at least stoichiometric quantities relative to the amount of N-functionalized product that is produced. Typically, when the oxidizing electrophile is present in at least a stoichiometric quantity relative to the N-functionalized product, an oxidizing regeneration reagent is not present in the reaction. In other embodiments, the oxidizing electrophile is present in a sub-stoichiometric quantity relative to the hydrocarbon. Typically, when the oxidizing electrophile is present in a sub-stoichiometric quantity, an oxidizing regeneration reagent and optionally an oxidative catalyst are present to regenerate the oxidizing electrophile from the reduced form of the oxidizing electrophile. In some preferred embodiments, the oxidizing electrophile is present in at least a stoichiometric quantity relative to the N-functionalized product and an oxidizing regeneration reagent and optionally an oxidative catalyst are not required, but can be present in the solvent (e.g., non-oxidizable liquid). In other preferred embodiments, the oxidizing electrophile is present in a sub-stoichiometric quantity relative to the hydrocarbon and an oxidizing reagent or an oxidative catalyst are present.

In some embodiments, the reduced form of the oxidizing electrophile is present in at least stoichiometric quantities relative to the N-functionalized product. In some embodiments, the reduced form of the oxidizing electrophile is present in a sub-stoichiometric quantity relative to the hydrocarbon. In some embodiments, the reduced form of the oxidizing electrophile is generated in situ from the reduction of the oxidizing electrophile upon formation of the nitrogen-functionalized product. In these instances, the reduced form of the oxidizing electrophile is used to regenerate the oxidizing electrophile. In some embodiments, the reduced form of the oxidizing electrophile is provided directly to the process for converting a hydrocarbon comprising at least one C—H bond to a nitrogen-functionalized product. In these instances, the reduced form of the oxidizing electrophile is used to generate the oxidizing electrophile. Accordingly, when the reduced form of the oxidizing electrophile is provided directly to the process in at least stoichiometric quantities or sub-stoichiometric quantities, the oxidant is present in the reaction mixture to generate the oxidizing electrophile.

Thus, the process for converting a hydrocarbon comprising at least one C—H bond to an N-functionalized product can comprise the oxidizing electrophile, the reduced form of the oxidizing electrophile, or both the oxidizing electrophile and the reduced form of the oxidizing electrophile. The amount of the oxidizing electrophile and/or the reduced form of the oxidizing electrophile is not particularly limited such that a sufficient amount of the oxidizing electrophile exists to convert the hydrocarbon to the N-functionalized product. Accordingly, the oxidizing electrophile and/or reduced form of the oxidizing electrophile can be present in an amount of about 0.01 mol % of the hydrocarbon or more (e.g., about 0.015 mol % or more, about 0.02 mol % or more, about 0.04 mol % or more, about 0.06 mol % or more, about 0.08 mol % or more, about 0.1 mol % or more, about 0.2 mol % or more, about 0.3 mol % or more, about 0.4 mol % or more, about 0.5 mol % or more, about 1 mol % or more, about 2 mol % or more, about 3 mol % or more, about 5 mol % or more, about 10 mol % or more, about 20 mol % or more, about 50 mol % or more, or about 100 mol % or more). Alternatively, or in addition, the oxidizing electrophile and/or the reduced form of the oxidizing electrophile can be present in an amount of about 2000 mol % of the hydrocarbon or less (e.g., about 1500 mol % or less, about 1000 mol % or less, about 900 mol % or less, about 800 mol % or less, about 700 mol % or less, about 600 mol % or less, about 500 mol % or less, about 400 mol % or less, about 300 mol % or less, about 200 mol % or less, or about 100 mol % or less). Any two of the foregoing endpoints can be used to define a close-ended range, or any single endpoint can be used singly to define an open-ended range. For example, the oxidizing electrophile and/or the reduced form of the oxidizing electrophile can be present in an amount between about 0 mol % to about 2000 mol % of the hydrocarbon, for example, about 0 mol % to about 1500 mol %, about 0 mol % to about 1000 mol %, about 0 mol % to about 900 mol %, about 0 mol % to about 800 mol %, about 0 mol % to about 700 mol %, about 0 mol % to about 600 mol %, about 0 mol % to about 500 mol %, about 0 mol % to about 400 mol %, about 0 mol % to about 300 mol %, about 0 mol % to about 200 mol %, about 0 mol % to about 100 mol %, about 0.1 mol % to about 100 mol %, about 0.2 mol % to about 100 mol %, about 0.3 mol % to about 100 mol %, about 0.4 mol % to about 100 mol %, about 0.5 mol % to about 100 mol %, about 1 mol % to about 100 mol %, about 2 mol % to about 100 mol %, about 3 mol % to about 100 mol %, about 5 mol % to about 100 mol %, about 10 mol % to about 100 mol %, about 20 mol % to about 100 mol %, about 50 mol % to about 100 mol %, about 100 mol % to about 100 mol %, or about 100 mol % to about 600 mol %.

The oxidizing electrophile and reduced form of the oxidizing electrophile comprise at least one nitrogen-containing ligand. The nitrogen-containing ligand can be any suitable nitrogen-based compound such that the conjugate acid has an experimental or theoretical pKa in water of less than about 14 (e.g., less than about 13, less than about 12, less than about 11, less than about 10, less than about 9, less than about 8, less than about 7, less than about 6, less than about 5, less than about 4, less than about 3, less than about 2, less than about 1, less than about 0, less than about −1, less than about −2, less than about −3, less than about −4, less than about −5, less than about −6, less than about −7, less than about −8, less than about 9, or less than about −10). In certain embodiments, the conjugate acid of the nitrogen-based compound has an experimental or theoretical pKa in water of less than about 10, preferably less than about 4.

In some embodiments, the at least one nitrogen containing compound has the formula —$NH_nY_{2-n}$, wherein Y is an electron withdrawing group and n is 0 or 1. In certain embodiments, n is 0. In some embodiments, Y is aryl (e.g., deactivated aryl), —F, —COR, —C(O)OR, —C(O)NRR', —$NO_2$, —NO, —$CH_2SO_2$, —$SO_2R$, —$SO_2F$, —$SO_2OH$, —$SO_2NH_2$, or —P(O)RR', wherein R and R' are the same or different and each is aliphatic, heteroaliphatic, aromatic, or heteroaromatic. In certain embodiments, Y is —COR, —C(O)OR, —C(O)NRR', or —$SO_2R$, wherein R and R' are the same or different and each is aliphatic, heteroaliphatic, aromatic, or heteroaromatic. In some instances, Y is a perfluorinated moiety (e.g., —COCF$_3$, —COC$_6$F$_5$, or —SO$_2$CF$_3$).

As used herein, "aliphatic" refers to a substituted or unsubstituted C$_1$-C$_9$ alkyl substituent, in which, "C$_1$-C$_9$ alkyl" refers to an alkyl carbon chain from 1 to 9 (i.e., 1, 2, 3, 4, 5, 6, 7, 8, or 9) carbons in length. In some embodiments, C$_1$-C$_9$ alkyl can be saturated, unsaturated, branched, straight-chained, cyclic, or a combination thereof. An exemplary, but non-limiting list of C$_1$-C$_9$ alkyl aliphatics includes methyl, ethyl, n-propyl, iso-propyl, n-butyl, sec-butyl, tert-butyl, n-pentyl, sec-pentyl, neo-pentyl, hexyl, heptyl, octyl, nonyl, cyclopentyl, cyclohexyl, propenyl, 2-butenyl, 3-butenyl, 2-pentenyl, 3-pentenyl, 4-pentenyl, or a combination thereof. In certain embodiments, the aliphatic group is perfluorinated.

As used herein, "heteroaliphatic" refers to refers to a substituted or unsubstituted C$_1$-C$_9$ alkyl substituent which contains at least 1 heteroatom (e.g., O, S, N, and/or P) in the core of the molecule (i.e., the carbon backbone). In certain instances, the heteroaliphatic substituent has at least 2 heteroatoms in the core of the molecule (e.g., at least 3, 4, 5, or 6 heteroatoms in the core of the molecule). In some embodiments, the heteroaliphatic compound is an ether, an ester, a carbonate, an amide, an amine, a carbamate, a thioether, a thioester, a phosphate, a heterocycloalkane, or a combination thereof. In certain embodiments, the heteroaliphatic group is perfluorinated.

As used herein, "aromatic" refers to a substituted or unsubstituted, monocyclic or polycyclic (e.g., bicyclic, tricyclic) aromatic substituent. The aromatic substituent can be any suitable aromatic substituent. An exemplary, but non-limiting list of aromatic substituents includes phenyl, xylenyl, naphthyl, biphenyl, anthracyl, or a combination thereof. In certain embodiments, the aromatic group is perfluorinated.

As used herein, "heteroaromatic" refers to a substituted or unsubstituted, monocyclic or polycylic (e.g., bicyclic, tricyclic) aromatic compound which has at least one heteroatom (e.g., O, S, or N) in at least one of the rings. In certain embodiments, the heteroaromatic substituent is polycyclic and has from 2 to 4 aromatic rings (i.e., 2, 3, or 4). Each ring of the heteroaromatic substituent containing a heteroatom can contain one or two oxygen and/or sulfur atoms and/or from one to four nitrogen atoms, provided that the total number of heteroatoms in each ring is 4 or less and each ring has at least one carbon atom. The fused rings completing the bicyclic and tricyclic groups can contain only carbon atoms and can be saturated, partially saturated, or unsaturated. The nitrogen and sulfur atoms can optionally be oxidized, and the nitrogen atoms can optionally be quaternized. Heteroaromatic substituents that are bicyclic or tricyclic must include at least one fully aromatic ring but the other fused ring(s) can be aromatic or non-aromatic. In some embodiments, the heteroaromatic substituent is or comprises pyrrolyl, isoindolyl, indolizinyl, indolyl, furanyl, benzofuranyl, benzothiophenyl, thiophenyl, pyridyl, acridinyl, naphthyridinyl, quinolinyl, isoquinolinyl, isoxazolyl, oxazolyl, benzoxazolyl, isothiazolyl, thiazolyl, benzthiazolyl, imidazolyl, thiadiazolyl, tetrazolyl, triazolyl, oxadiazolyl, benzimidazolyl, purinyl, pyrazolyl, pyrazinyl, pteridinyl, quinoxalinyl, phthalazinyl, quinazolinyl, triazinyl, phenazinyl, cinnolinyl, pyrimidinyl, pyridazinyl, or a combination thereof. In certain embodiments, the heteroaromatic group is perfluorinated.

As used herein, the term "substituted" can mean that one or more hydrogens on the designated atom or group are replaced with another group provided that the designated atom's normal valence is not exceeded. For example, when the substituent is oxo (i.e., =O), then two hydrogens bonded to the atom are replaced. In certain embodiments, the substituent is halo (e.g., fluoro, chloro, bromo, iodo), OH, cyano, nitro, alkoxy, amino, aryl, heteroaryl, alkyl, heteroalkyl, oxo, or combinations thereof. In certain embodiments, the substituent is fluoro. For example, the aliphatic, heteroaliphatic, aromatic, or heteroaromatic group can be fluorinated or perfluorinated. Combinations of substituents and/or variables are permissible provided that the substitutions do not significantly adversely affect synthesis or use of the compound. The substituted moiety typically comprises at least one substituent (e.g., 1, 2, 3, 4, 5, 6, etc.) in any suitable position (e.g., 1-, 2-, 3-, 4-, 5-, or 6-position, etc.).

In some embodiments, the oxidizing electrophile is of the formula $M^m(NH_nY_{2-n})_p$, wherein M is a main group or transition metal cation as described herein, Y is aryl (e.g., deactivated aryl), —F, —COR, —C(O)OR, —C(O)NRR', —NO$_2$, —NO, —CH$_2$SO$_2$, —SO$_2$R, —SO$_2$F, —SO$_2$OH, —SO$_2$NH$_2$, or —P(O)RR', in which R and R' are the same or different and each is aliphatic, heteroaliphatic, aromatic, or heteroaromatic, m is the formal oxidation state of M, n is 0 or 1, and p is 1 to m. Depending on M, m is an integer that ranges from 1 to 8 (i.e., 1, 2, 3, 4, 5, 6, 7, or 8). Preferably, m is from 3 to 6 (i.e., 3, 4, 5, or 6). When the oxidizing electrophile is of the formula $M^m(NH_nY_{2-n})_p$, Y preferably is —COR, —C(O)OR, —C(O)NRR', or —SO$_2$R, wherein R and R' are the same or different and each is aliphatic, heteroaliphatic, aromatic, or heteroaromatic. In some instances, Y is perfluorinated. Preferably, Y is —COCF$_3$, —COC$_6$F$_5$, or —SO$_2$CF$_3$.

Accordingly, in some embodiments, the reduced form of the oxidizing electrophile is of the formula $M^{m-2}(NH_nY_{2-n})_{p-2}$, in which M is a main group or transition metal cation, Y is aryl (e.g., deactivated aryl), —F, —COR, —C(O)OR, —C(O)NRR', —NO$_2$, —NO, —CH$_2$SO$_2$, —SO$_2$R, —SO$_2$F, —SO$_2$OH, —SO$_2$NH$_2$, or —P(O)RR', wherein R and R' are the same or different and each is aliphatic, heteroaliphatic, aromatic, or heteroaromatic, m is the formal oxidation state of M, n is 0 or 1, and p is 1 to m. In some embodiments, m is an integer from 1 to 8 (i.e., 1, 2, 3, 4, 5, 6, 7, or 8). In certain embodiments, depending on M, m is an integer that ranges from 3 to 6 (i.e., 3, 4, 5, or 6). In certain of these embodiments, Y is —COR, —C(O)OR, —C(O)NRR', or —SO$_2$R, wherein R and R' are the same or different and each is aliphatic, heteroaliphatic, aromatic, or heteroaromatic. In some instances, Y is perfluorinated (e.g., —COCF$_3$, —COC$_6$F$_5$, or —SO$_2$CF$_3$).

In some embodiments, the oxidizing electrophile and/or reduced form of the oxidizing electrophile further comprises one or more ligands beyond the at least one nitrogen-containing ligand to balance the net charge and/or solvate the oxidizing electrophile and/or reduced from of the oxidizing electrophile. The ligand can be any ligand that suitably coordinates to the transition metal or main group element (e.g., M). For example, each ligand can be a nitrogen-containing compound or a non-nitrogen-containing compound, the same or different, or anionic or neutral. In some embodiments, the one or more ligands are derived from the solvent. In some embodiments, each ligand (L) is independently an oxide (e.g., a bridging oxide (bridging oxo) or a terminal oxide (terminal oxo)), hydroxide, or combination thereof. In certain embodiments, the ligand is anionic and helps balance the charge of the oxidizing electrophile. In certain embodiments, the ligand is neutral and helps solvate the charge of the oxidizing electrophile. In some embodiments, the ligand is the solvent (e.g., a non-oxidizable liquid), a substrate molecule, a product of the substrate oxidation, or a combination thereof. Accordingly, in some embodiments, the oxidizing electrophile is of the formula $M_m(NH_nY_{2-n})_pL_q$, wherein M is a main group cation or transition metal cation, as described herein, L is a ligand, Y is aryl (e.g., deactivated aryl), —F, —COR, —C(O)OR, —C(O)NRR', —NO$_2$, —NO, —CH$_2$SO$_2$, —SO$_2$R, —SO$_2$F, —SO$_2$OH, —SO$_2$NH$_2$, or —P(O)RR', in which R and R' are the same or different and each is aliphatic, heteroaliphatic, aromatic, or heteroaromatic, m is the formal oxidation state of M, n is 0 or 1, p is 1 to m, and q is 0 to 5.

The oxidizing electrophile of the formula $M^m(NH_nY_{2-n})_pL_q$ can have any suitable net charge. For example, the oxidizing electrophile of the formula $M^m(NH_nY_{2-n})_pL_q$ can have a net charge of +5, +4, +3, +2, or +1, or a neutral net charge. In certain embodiments, the oxidizing electrophile of the formula $M^m(NH_nY_{2-n})_pL_q$ is a neutral species.

In some embodiments, the ligand is at least one monodentate or bidentate ligand that is aliphatic-based or aromatic-based and comprises at least one oxo, thiol, sulfonyl, or carboxyl group, and optionally comprises one or more electron withdrawing groups (e.g., —NO$_2$, fluoro-$C_{1-8}$ alkyl, —F, —OOCR, —COOH, —OH$_2^+$, —CONH$_2$, —COOR, —NR$_3^+$, —CN, —SO$_3$H, —SO$_3$R, —SO$_3$W, or a combination thereof, in which R is hydrogen or any aliphatic (e.g., $C_{1-8}$ alkyl, fluoro-$C_{1-8}$ alkyl), heteroaliphatic, aromatic, or heteroaromatic moiety, each of which is optionally substituted, and W is a cation comprising a metal selected from boron, bismuth, antimony, arsenic, lanthanum, cerium, scandium, yttrium, titanium, zirconium, hafnium, silver, zinc, cadmium, aluminum, gallium, indium, germanium, tin, phosphorus, an alkali metal, or an alkaline earth metal). In certain embodiments, the ligand comprises at least one carboxyl group. As used herein, "aliphatic-based" or "aromatic-based" refer to the ligand as a whole, and the ligand can be bound directly to the aliphatic or aromatic portion, or indirectly via at least one oxo, thiol, sulfonyl, or carboxyl group. The terms "aliphatic" and "aromatic" are as described herein.

In certain embodiments, the ligand is aromatic-based. Preferably, in embodiments where the ligand is aromatic-based, the ligand comprises at least one carboxyl group and/or at least one nitro group.

In certain embodiments, the ligand is a mono- or bidentate ligand selected from the group consisting of:

monodentate ligands

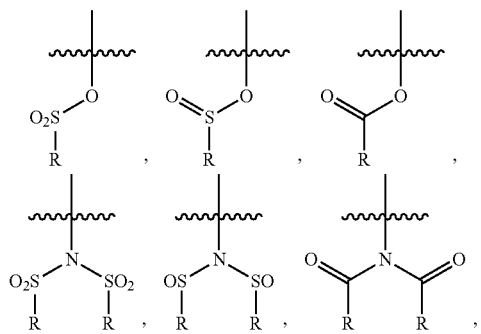

bidentate ligands

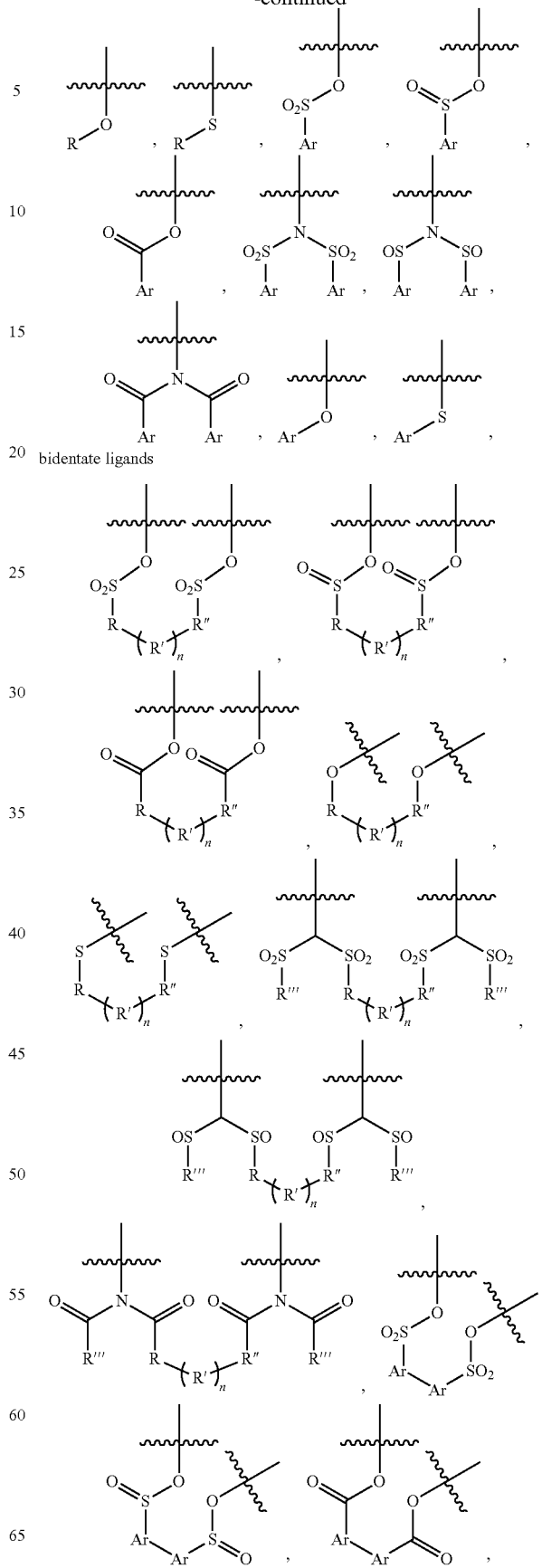

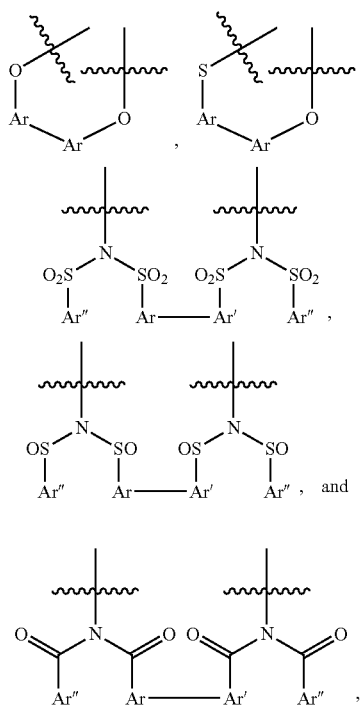

wherein R, R', R" and R'" are the same or different and each is an optionally substituted alkyl or heteroalkyl (e.g., a secondary or tertiary alkyl, a secondary or tertiary heteroalkyl), Ar, Ar', and Ar" are the same or different and each is an optionally substituted aryl (e.g., phenyl, deactivated aryl, as described herein), and n is 0 or an integer of 1 to 6. The alkyl, heteroalkyl, aryl, and substituents are as described herein.

The ligand also can be of the formula —Ar-EWG, wherein Ar is an optionally substituted aryl and EWG is at least one electron withdrawing group, as described herein. For example, the electron withdrawing group can be at least one moiety selected from —$NO_2$, fluoro-$C_{1-8}$ alkyl, —F, —OOCR, —COOH, —$OH_2^+$, —$CONH_2$, —COOR, —$NR_3^+$, —CN, —$SO_3H$, —$SO_3R$, —$SO_3W$, and a combination thereof. In the context of the electron withdrawing group, R is hydrogen or any aliphatic (e.g., $C_{1-8}$ alkyl, fluoro-$C_{1-8}$ alkyl), heteroaliphatic, aromatic, or heteroaromatic moiety, each of which is optionally substituted, and W is a cation comprising a metal selected from boron, bismuth, antimony, arsenic, lanthanum, cerium, scandium, yttrium, titanium, zirconium, hafnium, silver, zinc, cadmium, aluminum, gallium, indium, germanium, tin, phosphorus, an alkali metal, or an alkaline earth metal.

For example, the ligand can be:

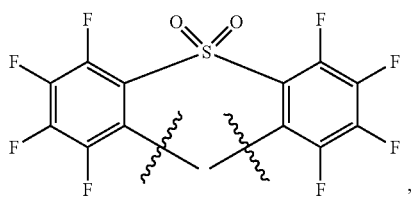

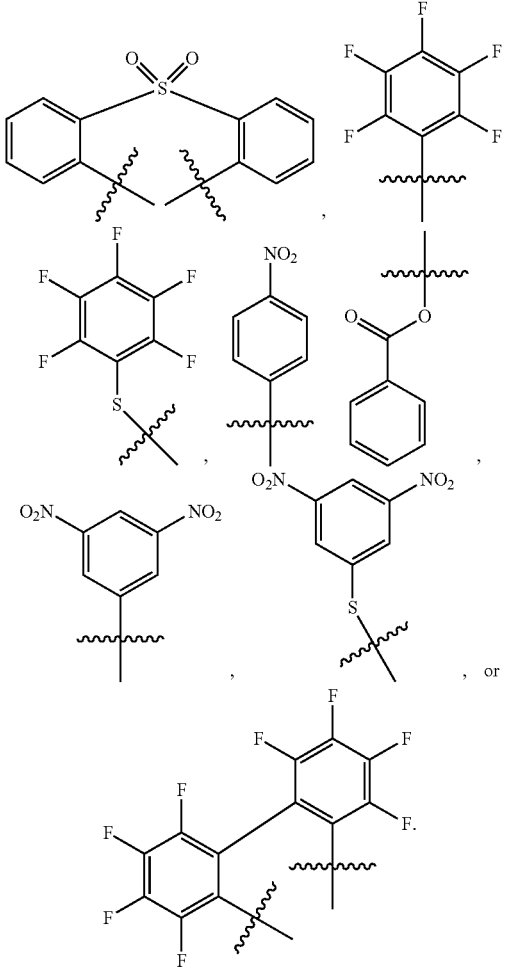

The ligand can be present in the mixture in less than stoichiometric quantities relative to the main group element, stoichiometric quantities relative to the main group element, or at least stoichiometric quantities relative to the main group element.

The process for converting a hydrocarbon comprising at least one C—H bond to an N-functionalized product comprises a solvent. The solvent can be any suitable solvent such that the solvent does not interfere with the process for converting a hydrocarbon comprising at least one C—H bond to an N-functionalized product. In certain embodiments, the solvent can be considered substantially inert under the reaction conditions, i.e., a non-oxidizable liquid. As used herein, "substantially inert" refers to a liquid (e.g., fluid or solvent) that maintains greater than about 80% stability in the presence of the oxidizing electrophile, such as measured by the retention of the solvent peaks in a $^1H$ Nuclear Magnetic Resonance (NMR) spectrum, relative to a standard. In certain embodiments, the liquid can maintain greater than about 85% stability in the presence of the oxidizing electrophile, for example, greater than about 90% stability in the presence of the oxidizing electrophile, greater than about 92% stability in the presence of the oxidizing electrophile, greater than about 94% stability in the presence of the oxidizing electrophile, greater than about 95% stability in the presence of the oxidizing electrophile, greater than about 98% stability in the presence of the oxidizing electrophile, or greater than about 99% stability in the presence of the oxidizing electrophile. Ideally, the liquid is totally inert to the oxidizing conditions but with strong oxidants, it can be expected that a small amount of liquid may be consumed or lost in subsequent recycle steps.

As used herein, the terms "liquid" or "liquid medium" refer to any medium that comprises a liquid. For example, the liquid or liquid medium can exist as a liquid-solid medium, a liquid-gas medium, a liquid-liquid medium, a liquid-gas-solid medium, etc. Accordingly, the liquid or liquid medium can be, for example, a solution, a gas-sparged liquid, a gel, a colloid, a slurry, a dispersion, an emulsion, or a combination thereof.

In some embodiments, the non-oxidizable liquid is a fluorinated hydrocarbon, a sulfone, a deactivated arene, a deactivated aliphatic, a deactivated heteroarene, a deactivated heteroaliphatic, or has the formula $HNY_2$ or $H_2NY$, in which Y is aryl (e.g., deactivated aryl), —F, —COR, —C(O)OR, —C(O)NRR', —$NO_2$, —NO, —$CH_2SO_2$, —$SO_2R$, —$SO_2F$, —$SO_2OH$, —$SO_2NH_2$, or —P(O)RR', and R and R' are the same or different and each is aliphatic, heteroaliphatic, aromatic, or heteroaromatic, as described herein. Any combination of the foregoing non-oxidizable liquids also can be used.

In some embodiments, the non-oxidizable liquid is one or more suitable fluorinated hydrocarbon(s). The fluorinated hydrocarbon can be at least one fluorinated or perfluorinated straight chain aliphatic comprising at least 2 carbons, for example, at least 3, 4, 5, 6, 7, 8, 9, 10, 11, 12, 13, 14, 15, or 16 carbons. Preferably, the fluorinated hydrocarbon is at least one fluorinated or perfluorinated cyclic aliphatic comprising at least 3 carbons, for example, at least 4, 5, 6, 7, 8, 9, or 10 carbons. In some embodiments, the fluorinated or perfluorinated cyclic aliphatic can be monocyclic, bicyclic, or tricyclic. The fluorinated hydrocarbon can be perfluorinated and is branched or straight, and either substituted or unsubstituted. Preferably, the fluorinated or perfluorinated straight chain aliphatic and/or the fluorinated or perfluorinated cyclic aliphatic is substituted with one or more aliphatic substituents. More preferably, the fluorinated hydrocarbon is perfluorinated.

Specific examples include perfluropentane, perfluorohexane, perfluoroheptane, perfluorooctane, perfluorononane, perfluorodecane, perfluorocyclohexane, perfluorocycloheptane, perfluorocyclooctane, perfluorodecalin, perfluoromethylcyclohexane, perfluorodimethylcyclohexane, perfluorotrimethylcyclohexane, perfluoroethylcyclohexane, perfluorodiethylcyclohexane, perfluorotriethylcyclohexane, perfluoroethylmethylcyclohexane, and perfluoro-2,2,3,3-tetramethylbutane.

In some embodiments, the non-oxidizable liquid is one or more sulfone(s) of the formula:

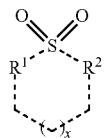

in which $R^1$ and $R^2$ are independently chosen from an aryl group and alkyl group, each of which is optionally substituted, the dashed lines represent optional bonds and atoms (e.g., C, N, O, S, or P), and x is an integer from 0 to 3 (i.e., 0, 1, 2, or 3). In certain embodiments, $R^1$ and $R^2$ are connected by a chain to produce a cyclic sulfone.

In some embodiments, the sulfone is at least one alkyl sulfone, in which both $R^1$ and $R^2$ are independently chosen as alkyl groups. The alkyl group can be any suitable straight chain, branched, or cyclic alkyl group (e.g., $C_{1-9}$ alkyl). In certain embodiments, the alkyl group is substituted with at least 1 electron withdrawing substituent (e.g., at least 2, 3, or 4 electron withdrawing substituents), such as those described herein. In certain embodiments, the alkyl groups are connected by an alkylene chain to produce a cyclic alkyl sulfone, such as sulfolane.

As used herein, "alkyl" refers to an aliphatic substituent that can be substituted, unsubstituted, branched, straight-chained, cyclic, or a combination thereof, and can be fully saturated or include portions that are unsaturated or aromatic. In some embodiments, the alkyl is $C_1$-$C_9$ alkyl, such as methyl, ethyl, n-propyl, iso-propyl, n-butyl, sec-butyl, tert-butyl, n-pentyl, sec-pentyl, neo-pentyl, hexyl, heptyl, octyl, nonyl, cyclopentyl, cyclohexyl, propenyl, 2-butenyl, 3-butenyl, 2-pentenyl, 3-pentenyl, 4-pentenyl, or a combination thereof.

In some embodiments, the alkyl is a heteroalkyl group, a cycloalkyl group, or a heterocycloalkyl group.

As used herein, "heteroalkyl" refers to a substituted or unsubstituted alkyl which contains at least 1 heteroatom (e.g., O, S, N, and/or P) in the core of the molecule (i.e., any part of the molecule except for the alkane-containing portion). Accordingly, at least 1 heteroatom can be a pendant substituent or part of a carbon chain. In certain instances, the heteroalkyl group has at least 2 heteroatoms in the core of the molecule (e.g., at least 3, 4, 5, or 6 heteroatoms in the core of the molecule). In some embodiments, the heteroalkyl group comprises a moiety selected from an ether, an ester, a carbonate, an amide, an amine, a carbamate, a thioether, a thioester, a phosphate, a heterocycloalkane, a haloalkane, an acetyl, an alcohol, a ketone, an aldehyde, a carboxylate, a carboxylic acid, a hemiacetal, an acetal, a ketal, an imine, and imide, a thiol, a disulfide, a sulfoxide, a thioketone, or a combination thereof.

The term "cycloalkyl," as used herein, refers to a substituted or unsubstituted alkyl group comprising a cyclic alkane moiety containing from, for example, 3 to 6 carbon atoms or from 5 to 6 carbon atoms. In some embodiments, the cycloalkyl group is cyclopropyl, cyclobutyl, cyclopentyl, or cyclohexyl. In some embodiments, the cycloalkyl can be a cycloalkenyl, as long as the cycloalkenyl comprises an alkane-containing portion. The term "cycloalkenyl" refers to a cycloalkane, as described herein, with at least one C—C double bond in the ring. For example, the cycloalkenyl can be cyclopentenyl or cyclohexenyl.

The term "heterocycloalkyl," as used herein, refers to an alkyl group comprising a cyclic alkane moiety containing from, for example, 3 to 6 carbon atoms or from 5 to 6 carbon atoms which contains at least 1 heteroatom (e.g., O, S, N, and/or P) in the core of the molecule (i.e., any part of the molecule except for the alkane-containing portion). Accordingly, at least 1 heteroatom can be a pendant substituent or encompassed in a cyclic chain. In certain instances, the heterocycloalkyl has at least 2 heteroatoms in the core of the molecule (e.g., at least 3, 4, 5, or 6 heteroatoms in the core of the molecule). In some embodiments, the heterocycloalkyl group comprises a moiety selected from an ether, an ester, a carbonate, an amide, an amine, a carbamate, a thioether, a thioester, a phosphate, a haloalkane, an acetyl, an alcohol, a ketone, an aldehyde, a carboxylate, a carboxylic acid, a hemiacetal, an acetal, a ketal, an imine, and imide, a thiol, a disulfide, a sulfoxide, a thioketone, or a combination thereof. An exemplary, but non-limiting list of heterocycloalkyl groups includes tetrahydrofuranyl, piperazinyl, morpholinyl, cyclohexanonyl, and 2-cyclohexylethanolyl.

As used herein, "aryl group" refers to any suitable substituted or unsubstituted aromatic or heteroaromatic group, as described herein. In some embodiments of the non-oxidizable liquid, the aryl group is deactivated, which means the aryl group is substituted with at least 1 electron withdrawing substituent, for example, at least 2, 3, or 4 electron withdrawing substituents, such as those described herein.

In some embodiments, the sulfone is a non-oxidizable liquid that contains a sulfonyl ($-SO_2$) functional group, such as (methylsulfonyl)benzene, (ethylsulfonyl)benzene, (propylsulfonyl)benzene, (isopropylsulfonyl)benzene, (butylsulfonyl)benzene, (methylsulfonyl)pyridine, (ethylsulfonyl)pyridine, (propylsulfonyl)pyridne, (isopropylsulfonyl)pyridine, (butylsulfonyl)pyridine, (cyclohexylsulfonyl)benzene, sulfonyldibenzene, dibenzothiophene 5,5-dioxide, 2,3-dihydrobenzothiophene 1,1-dioxide, or thiochromane 1,1-dioxide, each of which is substituted or unsubstituted.

In some embodiments, the sulfone is (methylsulfonyl)methane ("dimethyl sulfone"), (methylsulfonyl)ethane, tetrahydrothiophene 1,1-dioxide ("sulfolane"), tetrahydro-2H-thiopyran 1,1-dioxide, thietane 1,1-dioxide, (ethylsulfonyl)ethane, 1-(ethylsulfonyl)propane, 1-(propylsulfonyl)propane, 1-(propylsulfonyl)butane, 1-(butylsulfonyl)butane, 2-(ethylsulfonyl)propane, 2-(isopropylsulfonyl)propane, 1-(ethylsulfonyl)-2-methylpropane, 1-(methylsulfonyl)butane, 1-(ethylsulfonyl)butane, 1-(isopropylsulfonyl)-2-methylpropane, 1-(ethylsulfonyl)-2-methylpropane, 2-methyl-1-(methylsulfonyl)propane, 1-(isobutylsulfonyl)-2-methylpropane, 2-(tert-butylsulfonyl)-2-methylpropane, perfluorinated (methylsulfonyl)methane, perfluorinated (methylsulfonyl)ethane, perfluorinated tetrahydrothiophene 1,1-dioxide, perfluorinated tetrahydro-2H-thiopyran 1,1-dioxide, perfluorinated thietane 1,1-dioxide, perfluorinated (ethylsulfonyl)ethane, perfluorinated 1-(ethylsulfonyl)propane, perfluorinated 1-(propylsulfonyl)propane, perfluorinated 1-(propylsulfonyl)butane, perfluorinated 1-(butylsulfonyl)butane, perfluorinated 2-(ethylsulfonyl)propane, perfluorinated 2-(isopropylsulfonyl)propane, perfluorinated 1-(ethylsulfonyl)-2-methylpropane, perfluorinated 1-(methylsulfonyl)butane, perfluorinated 1-(ethylsulfonyl)butane, perfluorinated 1-(isopropylsulfonyl)-2-methylpropane, perfluorinated 1-(ethylsulfonyl)-2-methylpropane, perfluorinated 2-methyl-1-(methylsulfonyl)propane, perfluorinated 1-(isobutylsulfonyl)-2-methylpropane, or perfluorinated 2-(tert-butylsulfonyl)-2-methylpropane, each of which is substituted or unsubstituted.

In other embodiments, the sulfone is (methylsulfonyl)methane ("dimethyl sulfone"), (methylsulfonyl)ethane, tetrahydrothiophene 1,1-dioxide ("sulfolane"), tetrahydro-2H-thiopyran 1,1-dioxide, thietane 1,1-dioxide, perfluorinated (methylsulfonyl)methane, perfluorinated (methylsulfonyl)ethane, perfluorinated tetrahydrothiophene 1,1-dioxide, perfluorinated tetrahydro-2H-thiopyran 1,1-dioxide, or perfluorinated thietane 1,1-dioxide.

In some embodiments, the sulfone is at least one alkyl sulfone, in which both $R_1$ and $R_2$ are independently chosen as alkyl groups. The alkyl group can be any suitable straight chain, branched, or cyclic alkyl group (e.g., $C_{1-9}$ alkyl). In certain embodiments, the alkyl group is substituted with at least 1 electron withdrawing substituent (e.g., at least 2, 3, or 4 electron withdrawing substituents), such as those described herein. In certain embodiments, the alkyl groups are connected by an alkyl chain to produce a cyclic alkyl sulfone, such as sulfolane.

In some embodiments, the non-oxidizable liquid is one or more deactivated arene(s). As used herein, "deactivated arene" refers to at least one monocyclic or polycyclic aromatic compound that has 1 or more electron withdrawing substituents. In some embodiments, the arene compound has 2 or more electron withdrawing substituents, for example, 3 or more, 4 or more, 5 or more, or 6 or more electron withdrawing substituents. In some embodiments, each carbon of the deactivated arene has at least one electron withdrawing substituent. In certain embodiments, the deactivated arene is polycyclic and has 2, 3, or 4 aromatic rings and includes, e.g., benzene, toluene, xylene, naphthalene, biphenyl, and anthracene. The electron withdrawing substituent can be any suitable electron withdrawing substituent, such as those described herein.

An exemplary, but non-limiting list of deactivated arenes (e.g., deactivated benzenes) includes $C_6H_5(NO_2)$, $C_6H_5(CF_3)$, $C_6H_5F$, $C_6H_5(COOH)$, $C_6H_5(CONH_2)$, $C_6H_5(COOCF_3)$, $C_6H_5(OOCCF_3)$, $C_6H_5(CN)$, $C_6H_5(SO_3H)$, $C_6H_5(SO_3R)$, $C_6H_5(SO_3Q)$, m-$C_6H_4(NO_2)_2$, o-$C_6H_4(NO_2)_2$, p-$C_6H_4(NO_2)_2$, m-$C_6H_4(CF_3)_2$, o-$C_6H_4(CF_3)_2$, p-$C_6H_4(CF_3)_2$, m-$C_6H_4F_2$, o-$C_6H_4F_2$, p-$C_6H_4F_2$, m-$C_6H_4(COOH)_2$, o-$C_6H_4(COOH)_2$, p-$C_6H_4(COOH)_2$, m-$C_6H_4(CONH_2)_2$, o-$C_6H_4(CONH_2)_2$, p-$C_6H_4(CONH_2)_2$, m-$C_6H_4(COOCF_3)_2$, o-$C_6H_4(COOCF_3)_2$, p-$C_6H_4(COOCF_3)_2$, m-$C_6H_4(OOCCF_3)_2$, o-$C_6H_4(OOCCF_3)_2$, p-$C_6H_4(OOCCF_3)_2$, m-$C_6H_4(CN)_2$, o-$C_6H_4(CN)_2$, p-$C_6H_4(CN)_2$, m-$C_6H_4(SO_3H)_2$, o-$C_6H_4(SO_3H)_2$, p-$C_6H_4(SO_3H)_2$, m-$C_6H_4(SO_3R)_2$, o-$C_6H_4(SO_3R)_2$, p-$C_6H_4(SO_3R)_2$, m-$C_6H_4(SO_3Q)_2$, o-$C_6H_4(SO_3Q)_2$, p-$C_6H_4(SO_3Q)_2$, m-$C_6H_4(CF_3)(NO_2)$, o-$C_6H_4(CF_3)(NO_2)$, p-$C_6H_4(CF_3)(NO_2)$, m-$C_6H_4(CF_3)(F)$, o-$C_6H_4(CF_3)(F)$, p-$C_6H_4(CF_3)(F)$, m-$C_6H_4(CF_3)(COOH)$, o-$C_6H_4(CF_3)(COOH)$, p-$C_6H_4(CF_3)(COOH)$, m-$C_6H_4(CF_3)(CONH_2)$, o-$C_6H_4(CF_3)(CONH_2)$, p-$C_6H_4(CF_3)(CONH_2)$, m-$C_6H_4(CF_3)(CN)$, o-$C_6H_4(CF_3)(CN)$, p-$C_6H_4(CF_3)(CN)$, m-$C_6H_4(CF_3)(SO_3H)$, o-$C_6H_4(CF_3)(SO_3H)$, p-$C_6H_4(CF_3)(SO_3H)$, m-$C_6H_4(CF_3)(SO_3R)$, o-$C_6H_4(CF_3)(SO_3R)$, p-$C_6H_4(CF_3)(SO_3R)$, m-$C_6H_4(CF_3)(SO_3Q)$, o-$C_6H_4(CF_3)(SO_3Q)$, p-$C_6H_4(CF_3)(SO_3Q)$, m-$C_6H_4(F)(NO_2)$, o-$C_6H_4(F)(NO_2)$, p-$C_6H_4(F)(NO_2)$, m-$C_6H_4(COOH)(NO_2)$, o-$C_6H_4(COOH)(NO_2)$, p-$C_6H_4(COOH)(NO_2)$, m-$C_6H_4(CONH_2)(NO_2)$, o-$C_6H_4(CONH_2)(NO_2)$, p-$C_6H_4(CONH_2)(NO_2)$, m-$C_6H_4(COOCF_3)(NO_2)$, o-$C_6H_4(COOCF_3)(NO_2)$, p-$C_6H_4(COOCF_3)(NO_2)$, m-$C_6H_4(OOCCF_3)(NO_2)$, o-$C_6H_4(OOCCF_3)(NO_2)$, p-$C_6H_4(OOCCF_3)(NO_2)$, m-$C_6H_4(CN)(NO_2)$, o-$C_6H_4(CN)(NO_2)$, p-$C_6H_4(CN)(NO_2)$, m-$C_6H_4(SO_3H)(NO_2)$, o-$C_6H_4(SO_3H)(NO_2)$, p-$C_6H_4(SO_3H)(NO_2)$, m-$C_6H_4(SO_3R)(NO_2)$, o-$C_6H_4(SO_3R)(NO_2)$, p-$C_6H_4(SO_3R)(NO_2)$, m-$C_6H_4(SO_3Q)(NO_2)$, o-$C_6H_4(SO_3Q)(NO_2)$, p-$C_6H_4(SO_3Q)(NO_2)$, 1,2,3-$C_6H_3(CF_3)_2(NO_2)$, 1,3,4-$C_6H_3(CF_3)_2(NO_2)$, 1,3,5-$C_6H_3(CF_3)_2(NO_2)$, 1,2,3-$C_6H_3(CF_3)(NO_2)_2$, 1,3,4-$C_6H_3(CF_3)(NO_2)_2$, 1,3,5-$C_6H_3(CF_3)(NO_2)_2$, 1,2,3-$C_6H_3F_2(NO_2)$, 1,3,4-$C_6H_3F_2(NO_2)$, 1,3,5-$C_6H_3F_2(NO_2)$, 1,2,3-$C_6H_3(CF_3)F_2$, 1,3,4-$C_6H_3(CF_3)F_2$, 1,3,5-$C_6H_3(CF_3)F_2$, 1,2,3-$C_6H_3(COOH)_2(NO_2)$, 1,3,4-$C_6H_3(COOH)_2(NO_2)$, 1,3,5-$C_6H_3(COOH)_2(NO_2)$, 1,2,3-$C_6H_3(CF_3)(COOH)_2$, 1,3,4-$C_6H_3(CF_3)(COOH)_2$, 1,3,5-$C_6H_3(CF_3)(COOH)_2$, 1,2,3-$C_6H_3(CONH_2)_2(NO_2)$, 1,3,4-$C_6H_3(CONH_2)_2(NO_2)$, 1,3,5-$C_6H_3(CONH_2)_2(NO_2)$, 1,2,3-$C_6H_3(CF_3)(CONH_2)_2$, 1,3,4-$C_6H_3(CF_3)(CONH_2)_2$, 1,3,5-$C_6H_3(CF_3)(CONH_2)_2$, 1,2,3-$C_6H_3(COOCF_3)_2(NO_2)$, 1,3,4-$C_6H_3(COOCF_3)_2(NO_2)$, 1,3,5-$C_6H_3(COOCF_3)_2(NO_2)$, 1,2,3-$C_6H_3(CF_3)(COOCF_3)_2$, 1,3,4-$C_6H_3(CF_3)(COOCF_3)_2$, 1,3,5-$C_6H_3(CF_3)(COOCF_3)_2$, 1,2,3-$C_6H_3(OOCCF_3)_2(NO_2)$, 1,3,4-$C_6H_3(OOCCF_3)_2(NO_2)$, 1,3,5-$C_6H_3(OOCCF_3)_2(NO_2)$, 1,2,3-$C_6H_3(CF_3)(OOCCF_3)_2$, 1,3,4-$C_6H_3(CF_3)$ (OOCCF$_3$)$_2$, 1,3,5-C$_6$H$_3$(CF$_3$)(OOCCF$_3$)$_2$, 1,2,3-C$_6$H$_3$(CN)$_2$(NO$_2$), 1,3,4-C$_6$H$_3$(CN)$_2$(NO$_2$), 1,3,5-C$_6$H$_3$(CN)$_2$(NO$_2$), 1,2,3-C$_6$H$_3$(SO$_3$H)(CN)$_2$, 1,3,4-C$_6$H$_3$(SO$_3$H)(CN)$_2$, 1,3,5-C$_6$H$_3$(SO$_3$H)(CN)$_2$, 1,2,3-C$_6$H$_3$(SO$_3$R)(CN)$_2$, 1,3,4-C$_6$H$_3$(SO$_3$R)(CN)$_2$, 1,3,5-C$_6$H$_3$(SO$_3$R)(CN)$_2$, 1,2,3-C$_6$H$_3$(SO$_3$Q)(CN)$_2$, 1,3,4-C$_6$H$_3$(SO$_3$Q)(CN)$_2$, 1,3,5-C$_6$H$_3$(SO$_3$Q)(CN)$_2$, 1,2,3-C$_6$H$_3$(CF$_3$)$_2$(SO$_3$H), 1,3,4-C$_6$H$_3$(CF$_3$)$_2$(SO$_3$H), 1,3,5-C$_6$H$_3$(CF$_3$)$_2$(SO$_3$H), 1,2,3-C$_6$H$_3$(CF$_3$)$_2$(SO$_3$R), 1,3,4-C$_6$H$_3$(CF$_3$)$_2$(SO$_3$R), 1,3,5-C$_6$H$_3$(CF$_3$)$_2$(SO$_3$R), 1,2,3-C$_6$H$_3$(CF$_3$)$_2$(SO$_3$Q), 1,3,4-C$_6$H$_3$(CF$_3$)$_2$(SO$_3$Q), 1,3,5-C$_6$H$_3$(CF$_3$)$_2$(SO$_3$Q), 1,2,3-C$_6$H$_3$(CF$_3$)$_3$, 1,3,4-C$_6$H$_3$(CF$_3$)$_3$, 1,3,5-C$_6$H$_3$(CF$_3$)$_3$, 1,2,3-C$_6$H$_3$(NO$_2$)$_3$, 1,3,4-C$_6$H$_3$(NO$_2$)$_3$, 1,3,5-C$_6$H$_3$(NO$_2$)$_3$, 1,2,3-C$_6$H$_3$F$_3$, 1,3,4-C$_6$H$_3$F$_3$, 1,3,5-C$_6$H$_3$F$_3$, 1,2,3-C$_6$H$_3$(COOH)$_3$, 1,3,4-C$_6$H$_3$(COOH)$_3$, 1,3,5-C$_6$H$_3$(COOH)$_3$, 1,2,3-C$_6$H$_3$(COOCF$_3$)$_3$, 1,3,4-C$_6$H$_3$(COOCF$_3$)$_3$, 1,3,5-C$_6$H$_3$(COOCF$_3$)$_3$, 1,2,3-C$_6$H$_3$(OOCCF$_3$)$_3$, 1,3,4-C$_6$H$_3$(OOCCF$_3$)$_3$, 1,3,5-C$_6$H$_3$(OOCCF$_3$)$_3$, 1,2,3-C$_6$H$_3$(CN)$_3$, 1,3,4-C$_6$H$_3$(CN)$_3$, 1,3,5-C$_6$H$_3$(CN)$_3$, 1,2,3-C$_6$H$_3$(SO$_3$H)$_3$, 1,3,4-C$_6$H$_3$(SO$_3$H)$_3$, 1,3,5-C$_6$H$_3$(SO$_3$H)$_3$, 1,2,3-C$_6$H$_3$(SO$_3$R)$_3$, 1,3,4-C$_6$H$_3$(SO$_3$R)$_3$, 1,3,5-C$_6$H$_3$(SO$_3$R)$_3$, 1,2,3-C$_6$H$_3$(SO$_3$Q)$_3$, 1,3,4-C$_6$H$_3$(SO$_3$Q)$_3$, 1,3,5-C$_6$H$_3$(SO$_3$Q)$_3$, 1,2,3-C$_6$H$_3$(CONH$_2$)$_3$, 1,3,4-C$_6$H$_3$(CONH$_2$)$_3$, and 1,3,5-C$_6$H$_3$(CONH$_2$)$_3$. As used herein, R is any aliphatic (e.g., $C_1$-8 alkyl, fluoro-$C_1$-8 alkyl), heteroaliphatic, aromatic, or heteroaromatic moiety, each of which is optionally substituted, and Q refers to a cation.

In certain embodiments, the non-oxidizable liquid is a nitroarene. As used herein, "nitroarene" refers to any deactivated arene comprising at least one nitro group. For example, the nitroarene can be nitro-substituted benzene, nitro-substituted toluene, nitro-substituted xylene, nitro-substituted naphthalene, nitro-substituted biphenyl, or nitro-substituted anthracene.

In some embodiments, the non-oxidizable liquid is one or more deactivated aliphatic(s). As used herein, "deactivated aliphatic" refers to at least one aliphatic group, as described herein, that has 1 or more electron withdrawing substituents (e.g., 2 or more, 3 or more, 4 or more, or 5 or more electron withdrawing substituents).

In some embodiments, the deactivated aliphatic non-oxidizable liquid is at least one saturated, unsaturated, branched, straight-chained, or cyclic $C_1$-$C_9$ alkyl aliphatic group that is substituted with at least 1 electron withdrawing substituent (e.g., 2 or more, 3 or more, 4 or more, or 5 or more electron withdrawing substituents). An exemplary, but non-limiting list of deactivated $C_1$-$C_9$ alkyl aliphatics is methyl, ethyl, n-propyl, iso-propyl, n-butyl, sec-butyl, tert-butyl, n-pentyl, sec-pentyl, neo-pentyl, hexyl, heptyl, octyl, nonyl, cyclopentyl, cyclohexyl, propenyl, 2-butenyl, 3-butenyl, 2-pentenyl, 3-pentenyl, 4-pentenyl, or a combination thereof, in which the $C_1$-$C_9$ alkyl is substituted with 1 or more electron withdrawing substituents.

In some instances, the deactivated aliphatic is methyl, ethyl, n-propyl, iso-propyl, n-butyl, sec-butyl, tert-butyl, n-pentyl, sec-pentyl, or neo-pentyl, in which the methyl, ethyl, n-propyl, iso-propyl, n-butyl, sec-butyl, tert-butyl, n-pentyl, sec-pentyl, or neo-pentyl is substituted with 1 or more electron withdrawing substituents. In certain embodiments, the deactivated aliphatic is methyl, ethyl, n-propyl, or iso-propyl in which the methyl, ethyl, n-propane, or iso-propyl is substituted with 1 or more electron withdrawing substituents.

In other embodiments, the deactivated aliphatic is trifluoromethanol, trifluoromethyl 2,2,2-trifluoroacetate, 2,2,2-trifluoroethan-1-ol, 2,2,2-trifluoroethyl 2,2,2-trifluoroacetate, perfluoroethyl 2,2,2-trifluoroacetate, 1,1,2,2,2-pentafluoroethan-1-ol, nitromethane, trifluoro(nitro)methane, 1,1,2,2-tetrafluoroethane-1,2-diol, 1,1,2,2-tetrafluoro-2-hydroxyethyl 2,2,2-trifluoroacetate, perfluoroethane-1,2-diylbis(2,2,2-trifluoroacetate), ethane-1,2-diylbis(2,2,2-trifluoroacetate), 1,1,2,2,3,3-hexafluoropropane-1,3-diol, propane-1,2,3-triyl tris(2,2,2-trifluoroacetate), oxalic acid, 1,1,1,4,4,4-hexafluorobutane-2,3-dione, methyl 2,2,2-trifluoroacetate, methyl 2,2,3,3,3-pentafluoropropanoate, or trifluoromethyl 2,2,3,3,3-pentafluoropropanoate.

In other embodiments, the deactivated aliphatic is trifluoromethyl acetate, 1,1-difluoroethyl acetate, 2,2,2-trifluoroethyl acetate, perfluoroethyl acetate, perfluoropropan-2-yl acetate, 1,1,1,3,3,3-hexafluoropropan-2-yl acetate, 1,1,2,2-tetrafluoro-2-hydroxyethyl acetate, perfluoroethane-1,2-diyl diacetate, ethane-1,2-diyl diacetate, propane-1,2,3-triyl trisacetate, perfluoropropane-1,2,3-triyl triacetate, 1,1,3,3-tetrafluoropropane-1,2,3-triyl triacetate, or 1,1-difluoroethane-1,2-diyl diacetate.

In some embodiments, the non-oxidizable liquid is one or more deactivated heteroarene(s). As used herein, "deactivated heteroarene" refers to at least one monocyclic or polycyclic heteroaromatic compound which has at least one heteroatom (O, S, or N) in at least one of the rings. The term "heteroaromatic" is as described herein.

In some embodiments, the deactivated heteroarene is isoxazole, oxazole, isothiazole, thiazole, imidazole, thiadiazole, tetrazole, triazole, oxadiazole, pyrazole, pyrazine, pyrimadine, or triazine, each of which is substituted or unsubstituted. In other preferred embodiments, the deactivated heteroarene is pyrrole, furan, thiophene, or pyridine, each of which is substituted with at least one substituent that is an electron withdrawing substituent.

In other embodiments, the deactivated heteroarene is perfluoroisoxazole, perfluorooxazole, perfluoroisothiazole, perfluorothiazole, perfluoroimidazole, perfluorothiadiazole, perfluorotetrazole, perfluorotriazole, perfluorooxadiazole, perfluoropyrazole, perfluoropyrazine, perfluorotriazine, perfluoropyrrole, perfluorofuran, perfluorothiophene, perfluoropyridine, nitropyrrole, nitrofuran, nitrothiophene, nitropyridine, cyanopyrrole, cyanofuran, cyanothiophene, cyanopyridine, picolinic acid, nicotinic acid, isonicotinic acid, pyridine sulfonic acid, pyrrole sulfonic acid, furan sulfonic acid, thiophene sulfonic acid, pyridine carboxylic acid, pyrrole carboxylic acid, furan carboxylic acid, thiophene carboxylic acid, trifluoromethyl pyridine, trifluoromethyl pyrrole, trifluoromethyl furan, or trifluoromethyl thiophene.

In some embodiments, the non-oxidizable liquid is one or more deactivated heteroaliphatic(s). The term "heteroaliphatic" is as described herein. In some embodiments, the heteroaliphatic compound is an ether, an ester, a carbonate, an amide, an amine, a carbamate, a thioether, a thioester, a phosphate, or a heterocycloalkane. The term "heterocycloalkane" refers to a cycloalkane, as described herein, in which at least one heteroatom (e.g., O, S, N, and/or P) replaces at least one carbon in the ring system. In an aspect, a heterocycloalkane is a 5-, 6-, or 7-membered monocyclic ring and contains one, two, or three heteroatoms selected from nitrogen, oxygen, and sulfur. Examples of such heterocycloalkane rings are pyrrolidine, pyrroline, pyran, piperidine, quinuclidine, imidazoline, dioxane, dioxolane, morpholine, thiomorpholine, trithiane, dithiane, pyrazoline, pyrazolidine, piperazine, or a combination thereof.

In certain embodiments, the deactivated heteroaliphatic has at least 1 electron withdrawing substituent. In some embodiments, the deactivated heteroaliphatic has at least 2 electron withdrawing substituents (e.g., at least 3, 4, 5, or 6 electron withdrawing substituents), such as those described herein.

For example, the deactivated heteroaliphatic compound can be trifluoro(trifluoromethoxy)methane, 1,1,1,2,2-pentafluoro-2-(trifluoromethoxy)ethane, 1,1,1,2,2-pentafluoro-2-(perfluoroethoxy)ethane, tris(trifluoromethyl)amine, 1,1,2,2,2-pentafluoro-N-(perfluoroethyl)-N-(trifluoromethyl)ethan-1-amine, tris(perfluoroethyl)amine, 2,2,2-trifluoro-N,N-bis(trifluoromethyl)acetamide, N,N-bis(trifluoromethyl)formamide, 2,2,2-trifluoroacetamide, perfluoropyrrolidine, perfluoropyrroline, perfluoropyran, perfluoropiperidine, perfluorodioxane, perfluoromorpholine, perfluoropiperazine, nitropyrrolidine, nitropyrroline, nitropyran, nitropiperidine, nitrodioxane, nitromorpholine, nitropiperazine, cyanopyrrolidine, cyanopyrroline, cyanopyran, cyanopiperidine, cyanodioxane, cyanomorpholine, cyanopiperazine, pyrrolidine carboxylic acid, pyrroline carboxylic acid, pyran carboxylic acid, piperidine carboxylic acid, dioxane carboxylic acid, morpholine carboxylic acid, piperazine carboxylic acid, pyrrolidine sulfonic acid, pyrroline sulfonic acid, pyran sulfonic acid, piperidine sulfonic acid, dioxane sulfonic acid, morpholine sulfonic acid, or piperazine sulfonic acid.

In some embodiments, the non-oxidizable liquid is one or more carbonate(s). The carbonate can be a chemical compound comprising at least one carbonate moiety (e.g., 1 carbonate, 2 carbonates, 3 carbonates, or 4 carbonates). For example, the carbonate can be an alkyl carbonate, a heteroalkyl carbonate, a cycloalkyl carbonate, a heterocycloalkyl carbonate, an aryl carbonate, hydrogen carbonate, or a combination thereof.

In certain embodiments, the non-oxidizable liquid has the formula $HNY_2$ or $H_2NY$, wherein Y is aryl (e.g., deactivated aryl), —F, —COR, —C(O)OR, —C(O)NRR', —$NO_2$, —NO, —$CH_2SO_2$, —$SO_2R$, —$SO_2F$, —$SO_2OH$, —$SO_2NH_2$, or —P(O)RR', and R and R' are the same or different and each is aliphatic, heteroaliphatic, aromatic, or heteroaromatic, as described herein. In certain embodiments, Y is —COR, —C(O)OR, —C(O)NRR', or —$SO_2R$. In some instances, Y is perfluorinated (e.g., —$COCF_3$, —$COC_6F_5$, —$SO_2CF_3$).

In any of the embodiments described herein, the electron withdrawing substituent can be any suitable electron withdrawing group, such as —$NO_2$, fluoro-$C_{1-8}$ alkyl, —F, —OOCR, —COOH, —$OH_2^+$, —$CONH_2$, —COOR, —$NR_3^+$, —CN, —$SO_3H$, —$SO_3R$, —$SO_3W$, or a combination thereof, in which R is hydrogen or any aliphatic (e.g., $C_{1-8}$ alkyl, fluoro-$C_{1-8}$ alkyl), heteroaliphatic, aromatic, or heteroaromatic, each of which is optionally substituted, and W is a cation comprising a metal selected from boron, bismuth, antimony, arsenic, lanthanum, cerium, scandium, yttrium, titanium, zirconium, hafnium, silver, zinc, cadmium, aluminum, gallium, indium, germanium, tin, phosphorus, an alkali metal, or an alkaline earth metal. In certain embodiments, R is —$CF_3$.

The process provides a nitrogen-functionalized product and an electrophile reduction product. The N-functionalized product can be any product that forms in which at least one C—H bond of the hydrocarbon substrate has been nitrogen-functionalized (e.g., mono-N-substituted product). For example, at least 2, 3, 4, 5, or 6 C—H bonds of the hydrocarbon can be nitrogen-functionalized thereby forming a di-N-substituted or poly-N-substituted product. Preferably, a monofunctionalized and/or difunctionalized product is formed. In some embodiments, the nitrogen-functionalized product becomes further substituted with other substituents.

As used herein, "nitrogen-functionalized product" refers to any hydrocarbon substrate with at least one C—H bond, in which the hydrogen atom has been replaced with a nitrogen atom. In some embodiments, the nitrogen atom is further substituted with one or two non-hydrogen substituents (Y). In such embodiments, a hydrogen on the hydrocarbon has been replaced with a substituent of the formula —$NH_nY_{2-n}$, in which Y and n are as defined herein. It is possible that in some embodiments, the nitrogen-functionalized product can further form an amine (e.g., $NH_2$-containing moiety) without any additional reactants.

In some embodiments, the process comprises separating the nitrogen-functionalized product and the electrophile reduction product by any suitable method. For example, the N-functionalized product and the electrophile reduction product can be separated by filtration, distillation, column chromatography, crystallization, centrifugation, extraction, recrystallization, or a combination thereof.

In some instances, the process further comprises converting the N-functionalized product to an amine. Depending on the hydrocarbon substrate, the amine can be a monoamine, a diamine, a polyamine, or a combination thereof. In certain embodiments, the amine comprises a monoamine, a diamine, or both a monoamine, and a diamine. Along with the amine production step, the at least one nitrogen-containing ligand can be regenerated as part of the process or at a later step.

In some instances, the formation of an amine can occur by a deprotection step, including contacting the nitrogen-functionalized product in an appropriate acid or base. Methods of deprotection are well known in the art, including the methods described in Wuts, Peter G. M., *Greene's Protective Groups in Organic Synthesis*, New York, Wiley-Interscience, 2014, the contents of which are incorporated by reference. In other instances, the process further comprises contacting the nitrogen-functionalized product with a compound of the formula H-Nu to form an amine, in which Nu is a nucleophilic group that enables the formation of the amine. The nitrogen-functionalized product can be contacted with a compound of the formula H-Nu before or after separation from the electrophile reduction product. For example, the mixture of the nitrogen-functionalized product and the electrophile reduction product can be contacted with H-Nu, followed by optional separation of the resulting amine from the electrophile reduction product. Alternatively, the nitrogen-functionalized product can be separated from the electrophile reduction product and then contacted with H-Nu. In some embodiments, the amine is further purified using techniques known in the art.

As used herein, "the compound of the formula H-Nu" refers to any compound comprising a nucleophile ("Nu") such that the compound of the formula H-Nu converts the substituent of the formula —$NH_nY_{2-n}$ to the substituent of the formula —$NH_2$. In some embodiments, H-Nu can be a charged species (for example, $[H-Nu]^{-1}$ or $[H-Nu]^{-2}$), such that Nu can be a neutral or charged species. In certain embodiments, H-Nu is a neutral species. In some embodiments, Nu is oxide, hydroxide, alkoxide, aryloxide, carboxylate, thiolate, bisulfide, optionally protected amide, or optionally protected azanide. Nitrogen protecting groups include, e.g., 9-fluorenylmethyl carbamyl (Fmoc), t-butyl carbamyl (BOC), benzyl carbamyl (Cbz), benzyl, benzylidenyl, triphenylmethyl, acetyl, trifluoroacetyl, phthalimidyl, and tosyl. Methods of protecting and deprotecting an amide or amine are known in the art and are described, for example, in Wuts, Peter G. M., *Greene's Protective Groups in Organic Synthesis, Fourth Edition*, New York, Wiley- Interscience, 2014, the contents of which are incorporated by reference. In some embodiments, Nu is —O, —OR$^1$, —CO$_2$R$^1$, —S, —SR$^1$, —NR$^1$, —NHR$^1$, or —NR$^1$R$^2$, in which R$^1$ and R$^2$ are the same or different and each is hydrogen, aliphatic, heteroaliphatic, aromatic, or heteroaromatic, as described herein. In some instances, H-Nu is NH$_3$, CH$_3$NH$_2$, PhNH$_2$, H$_2$O, CH$_3$OH, CH$_3$CH$_2$OH, or CH$_3$CO$_2$H. Preferably, H-Nu is NH$_3$.

In some embodiments, the process further comprises contacting the electrophile reduction product and any suitable oxidizing regeneration reagent to regenerate the oxidizing electrophile. The oxidizing regeneration reagent can be the same as or different from the oxidant. For example, the oxidizing regeneration reagent can be molecular oxygen, air, a peroxide, nitric oxide, nitrous oxide, nitric acid, sulfur trioxide, ozone, or a combination thereof. The oxidant can be used under an inert atmosphere, or in combination with air. The peroxide can be, e.g., an organic peroxide, inorganic peroxide, hydrogen peroxide, or a combination thereof. In some embodiments, the oxidant can be an organic oxidant. For example, the oxidant can be a quinone or a nitroxide. In certain embodiments, the oxidant is a quinone, molecular oxygen, air, a peroxide, nitric oxide, nitrous oxide, nitric acid, a nitroxide, sulfur trioxide, ozone, or a combination thereof.

Thus, the process for converting a hydrocarbon comprising at least one C—H bond to a nitrogen-functionalized product can comprise the oxidizing regeneration reagent, the oxidant, both the oxidizing regeneration reagent and the oxidant, or neither the oxidizing regeneration reagent nor the oxidant. Thus, the oxidizing regeneration reagent and the oxidant can be present in an amount of 0 mol % of the hydrocarbon. In some embodiments, the oxidizing regeneration reagent and/or the oxidant are present in the oxidizing composition. The amount of the oxidizing regeneration reagent and/or the oxidant is not particularly limited such that a sufficient amount of the oxidizing electrophile is maintained to convert the hydrocarbon to the N-functionalized product.

Accordingly, the oxidizing regeneration reagent and/or the oxidant can be present in an amount of about 0.01 mol % of the hydrocarbon or more (e.g., about 0.015 mol % or more, about 0.02 mol % or more, about 0.04 mol % or more, about 0.06 mol % or more, about 0.08 mol % or more, about 0.1 mol % or more, about 0.2 mol % or more, about 0.3 mol % or more, about 0.4 mol % or more, about 0.5 mol % or more, about 1 mol % or more, about 2 mol % or more, about 3 mol % or more, about 5 mol % or more, about 10 mol % or more, about 20 mol % or more, about 50 mol % or more, or about 100 mol % or more). Alternatively, or in addition, the oxidizing regeneration reagent and/or the oxidant can be present in an amount of about 2000 mol % of the hydrocarbon or less (e.g., about 1500 mol % or less, about 1000 mol % or less, about 900 mol % or less, about 800 mol % or less, about 700 mol % or less, about 600 mol % or less, about 500 mol % or less, about 400 mol % or less, about 300 mol % or less, about 200 mol % or less, or about 100 mol % or less). Any two of the foregoing endpoints can be used to define a close-ended range, or any single endpoint can be used singly to define an open-ended range.

In some embodiments, the oxidant and/or the oxidizing regeneration reagent require an oxidative catalyst to facilitate the generation and/or regeneration of the oxidizing electrophile. The oxidative catalyst can be any suitable catalyst, such as an oxidative catalyst that comprises copper, silver, iron, cobalt, manganese, nickel, chromium, vanadium, or a combination thereof.

The process for converting a hydrocarbon comprising at least one C—H bond to a nitrogen-functionalized product comprises the oxidizing electrophile and/or the reduced form of an oxidizing electrophile, and solvent (e.g., non-oxidizable liquid) as a heterogeneous mixture or a homogenous mixture. For example, the oxidizing electrophile and/or the reduced form of an oxidizing electrophile can be present in the solvent as a solid, a slurry, an emulsion, or a combination thereof. Alternatively, or in addition to, the oxidizing electrophile and/or the reduced form of an oxidizing electrophile can be soluble in the solvent. In certain embodiments, the oxidizing electrophile and/or the reduced form of an oxidizing electrophile are immobilized on a solid support contain within a reactor.

The process for converting a hydrocarbon comprising at least one C—H bond to a nitrogen-functionalized product can be carried out in a single reactor or carried out in at least 2 reactors (e.g., at least 3 or at least 4 reactors). When the process is carried out in a single reactor and the oxidizing electrophile is present in at least a stoichiometric quantity, the process for converting a hydrocarbon comprising at least one C—H bond to a nitrogen-functionalized product does not necessitate regeneration of the oxidizing electrophile. In this embodiment, the process for oxidizing a substrate can be carried out under a single set of conditions in the single reactor.

Alternatively, the process can be carried out in a single reactor, in which the reactor is operated under conditions suitable for converting the hydrocarbon using the oxidizing electrophile and simultaneous regeneration of the oxidizing electrophile by contacting the electrophile reduction product and the oxidizing regeneration reagent. For example, when the oxidizing electrophile is depleted, the oxidizing regeneration reagent, optionally in the presence of an oxidative catalyst, is present in the solvent to regenerate the oxidizing electrophile.

In some embodiments, the process can be carried out in a single reactor in a sequential manner. For example, the reactor can be operated first under conditions suitable for converting the hydrocarbon using the oxidizing electrophile, then subsequently operated under conditions suitable for regeneration of the oxidizing electrophile by contacting the electrophile reduction product and the oxidizing regeneration reagent. For example, the oxidizing electrophile can be immobilized within the reactor, in which first a mixture comprising the hydrocarbon is circulated, then, when the oxidizing electrophile is depleted, a mixture comprising the oxidizing regeneration reagent, optionally in the presence of an oxidative catalyst, is circulated to regenerate the oxidizing electrophile.

Alternatively, the process can be carried out in a two reactor circulating liquid phase system, in which the reaction of the hydrocarbon and the oxidizing electrophile is carried out in a first reactor, and the reaction of the electrophile reduction product and the oxidizing regeneration reagent used to regenerate the oxidizing electrophile is carried out in a second reactor.

The reaction can take place at any temperature suitable for forming the N-functionalized product. In some embodiments, the process for oxidizing a substrate can be performed at less than about 300° C., for example, less than 285° C., less than about 275° C., less than 260° C., less than about 250° C., less than about 225° C., less than about 200° C., less than about 150° C., or less than about 140° C. Alternatively, or in addition to, the process for oxidizing a substrate can be performed at greater than about 50° C., for example, greater than about 70° C., greater than about 80°

C., greater than about 100° C., greater than about 120° C., greater than about 140° C., greater than about 150° C., greater than about 160° C., greater than about 170° C., greater than about 180° C., greater than about 190° C., or greater than about 200° C. Any two of the foregoing endpoints can be used to define a close-ended range, or one endpoint can be used singly to define an open-ended range. Thus, the process can be performed at a temperature between about 50° C. to about 300° C., for example, about 50° C. to about to about 275° C., about 50° C. to about 250° C., about 50° C. to about 225° C., about 50° C. to about 200° C., about 70° C. to about 200° C., about 80° C. to about 200° C., about 70° C. to about 140° C., about 100° C. to about 200° C., about 120° C. to about 200° C., about 140° C. to about 200° C., about 150° C. to about 200° C., about 160° C. to about 200° C., about 170° C. to about 200° C., about 180° C. to about 200° C., about 190° C. to about 200° C., about 200° C. to about 300° C., about 200° C. to about 350° C., about 100° C. to about 300° C., or about 150° C. to about 250° C. In a preferred embodiment, the temperature is between about 50° C. to about 200° C., and more preferably, between about 70° C. to about 140° C.

The invention also provides an oxidizing composition comprising, consisting essentially of, or consisting of: (a) an oxidizing electrophile comprising a main group element or transition metal in oxidized form and at least one nitrogen-containing ligand; (b) a non-oxidizable liquid selected from the group consisting of a fluorinated hydrocarbon, a sulfone, a deactivated arene, a deactivated aliphatic, a deactivated heteroarene, a deactivated heteroaliphatic, a compound of the formula $HNY_2$ or $H_2NY$, and a combination thereof, wherein Y is an electron-withdrawing group; and (c) optionally one or more additives of the formula $Z_a(NH_nY_{2-n})_p$, wherein Z is a cation, Y is aryl (e.g., deactivated aryl), —F, —COR, —C(O)OR, —C(O)NRR', —$NO_2$, —NO, —$CH_2SO_2$, —$SO_2R$, —$SO_2F$, —$SO_2OH$, —$SO_2NH_2$, or —P(O)RR', in which R and R' are the same or different and each is aliphatic, heteroaliphatic, aromatic, or heteroaromatic. Subscripts "a," "n," and "p" denote the number of each element or cation present to form a neutral compound. In particular, a is 1 to 5 (i.e., 1, 2, 3, 4, or 5), n is 0 or 1, and p is 1 to 5 (i.e., 1, 2, 3, 4, or 5).

The oxidizing composition can comprise any suitable oxidizing electrophile comprising a main group element or transition metal in oxidized form and at least one nitrogen-containing ligand. Suitable oxidizing electrophiles will be readily apparent from the description set forth herein.

The oxidizing composition can comprise any suitable non-oxidizable liquid selected from the group consisting of a fluorinated hydrocarbon, a sulfone, a deactivated arene, a deactivated aliphatic, a deactivated heteroarene, a deactivated heteroaliphatic, a compound of the formula $HNY_2$ or $H_2NY$, and a combination thereof. Suitable non-oxidizable liquids will be readily apparent from the description set forth herein.

In certain embodiments of the present invention, the liquid medium and/or oxidizing composition comprises one or more additives. Depending on the embodiment, the additive can be a non-oxidizable liquid as described herein, a salt additive, a non-halide containing Lewis acid, water, and/or ammonia. Desirably, the additives can be used to provide a functional benefit to the reaction mixture (e.g., liquid medium and/or composition), such as solvation, solubilization, viscosity modification, and/or charge transfer.

In some embodiments, the additive is not present in the oxidizing composition. Thus, the additive can be present in an amount of 0 mol % of the oxidizing electrophile. In some embodiments, the one or more additives are present in the oxidizing composition. The amount of additive is not particularly limited such that the additive can be used in amounts that are a fraction of the amount of oxidizing electrophile or in amounts that are in large excess of the amount of oxidizing electrophile. The one or more additives can be present in an amount of about 0.1 mol % of the oxidizing electrophile or more (e.g., about 0.2 mol % or more, about 0.3 mol % or more, about 0.4 mol % or more, about 0.5 mol % or more, about 1 mol % or more, about 2 mol % or more, about 3 mol % or more, about 5 mol % or more, about 10 mol % or more, about 20 mol % or more, about 50 mol % or more, or about 100 mol % or more). Alternatively, or in addition, the one or more additives can be present in an amount of about 2000 mol % of the oxidizing electrophile or less (e.g., about 1500 mol % or less, about 1000 mol % or less, about 900 mol % or less, about 800 mol % or less, about 700 mol % or less, about 600 mol % or less, about 500 mol % or less, about 400 mol % or less, about 300 mol % or less, about 200 mol % or less, or about 100 mol % or less). Any two of the foregoing endpoints can be used to define a close-ended range, or can be used singly to define an open-ended range. Thus, the one or more additives can be present in an amount between about 0 mol % to about 2000 mol % of the oxidizing electrophile, for example, about 0 mol % to about 1500 mol %, about 0 mol % to about 1000 mol %, about 0 mol % to about 900 mol %, about 0 mol % to about 800 mol %, about 0 mol % to about 700 mol %, about 0 mol % to about 600 mol %, about 0 mol % to about 500 mol %, about 0 mol % to about 400 mol %, about 0 mol % to about 300 mol %, about 0 mol % to about 200 mol %, about 0 mol % to about 100 mol %, about 0.1 mol % to about 100 mol %, about 0.2 mol % to about 100 mol %, about 0.3 mol % to about 100 mol %, about 0.4 mol % to about 100 mol %, about 0.5 mol % to about 100 mol %, about 1 mol % to about 100 mol %, about 2 mol % to about 100 mol %, about 3 mol % to about 100 mol %, about 5 mol % to about 100 mol %, about 10 mol % to about 100 mol %, about 20 mol % to about 100 mol %, about 50 mol % to about 100 mol %, about 100 mol % to about 1000 mol %, or about 100 mol % to about 600 mol %.

Generally, the additive is one or more salt compounds of the formula $Z_a(NH_nY_{2-n})_p$, wherein Z is a cation, Y is an electron-withdrawing group, as described herein. For example, Y can be aryl (e.g., deactivated aryl), —F, —COR, —C(O)OR, —C(O)NRR', —$NO_2$, —NO, —$CH_2SO_2$, —$SO_2R$, —$SO_2F$, —$SO_2OH$, —$SO_2NH_2$, or —P(O)RR', in which R and R' are the same or different and each is aliphatic, heteroaliphatic, aromatic, or heteroaromatic, a is 1 to 5, n is 0 or 1, and p is 1 to 5. Suitable forms of Y will be readily apparent from the description set forth herein. In some embodiments, the additive of formula $Z_a(NH_nY_{2-n})_p$ further comprises one or more ligands selected from the group of an oxide (e.g., a bridging oxide or a terminal oxide), a hydroxide, or an anion of an oxoacid. As used herein, "oxoacid" refers to any organic acid or inorganic acid which contains hydrogen, oxygen, and at least one other element, in which the protic hydrogen is attached to oxygen.

Z can be any suitable cation in any suitable oxidation state. Typically, Z has an oxidation state of +5, +4, +3, +2, or +1.

In some embodiments, $Z_a(NH_nY_{2-n})_p$ is selected from a Brønsted acid, a salt, or a combination thereof. Accordingly, Z can be a proton, ammonium, a cation of an alkali metal, a cation of an alkaline earth metal, or a combination thereof. In some embodiments, Z is hydrogen or a cation of lithium, sodium, potassium, rubidium, cesium, francium, beryllium, magnesium, calcium, strontium, barium, or radium.

In some embodiments, $Z_a(NH_nY_{2-n})_p$ is any suitable non-halide containing Lewis acid, which is a strong electron pair acceptor. In embodiments where $Z_a(NH_nY_{2-n})_p$ is a Lewis acid, Z can be a cation of a transition metal, a cation of a rare-earth metal, a main group cation, or a combination thereof. In some embodiments, Z is a cation of boron, bismuth, antimony, arsenic, lanthanum, cerium, scandium, yttrium, titanium, zirconium, hafnium, silver, zinc, cadmium, aluminum, gallium, indium, germanium, tin, phosphorus, or a combination thereof. In certain embodiments, Z is In(III), Sc(III), Zn(II), Ti(IV), Al(III), Ga(III), B(III), Sb(III), Bi(III), or As(III).

In other embodiments, the salt additive is one or more compounds of the formula $Q_aZ_b$, in which Q is a cation, Z is a bridging oxide, a terminal oxide, a hydroxide, or an anion of the oxygen acid, a is an integer from 1 to 5 (i.e., 1, 2, 3, 4, or 5), b is an integer from 1 to 5 (i.e., 1, 2, 3, 4, or 5), and wherein a and b are the same or different and balance the oxidation states of Q and Z. In $Q_aZ_b$, Q can be any suitable cation in any suitable oxidation state. In some embodiments, Q can be a proton, ammonium, a cation of an alkali metal, a cation of an alkaline earth metal, a cation of a rare-earth metal, a main group element cation, or a combination thereof. In some embodiments, Q is hydrogen or a cation of lithium, sodium, potassium, rubidium, cesium, francium, beryllium, magnesium, calcium, strontium, barium, or radium. Typically, Q has an oxidation state of +5, +4, +3, +2, or +1.

As used herein, "oxygen acid" refers to any organic acid or inorganic acid which contains hydrogen, oxygen, and at least one other element, in which the protic hydrogen is attached to oxygen. Generally, the conjugate anion of an oxygen acid is selected from sulfite, sulfate, hydrogen sulfate, thiosulfate, nitrite, nitrate, phosphate, phosphite, hydrogen phosphate, dihydrogen phosphate, carbonate, hydrogen carbonate, oxalate, cyanate, isocyanate, chromate, dichromate, permanganate, carboxylate, sulfonate, borate, and any combination thereof.

In $Q_aZ_b$, Z can be any suitable oxide (e.g., a bridging oxide or a terminal oxide), hydroxide, or anion of an oxygen acid, as described herein, in any suitable oxidation state. In some embodiments, Z is an anion of the oxygen acid that is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, and heteroaromatic borate. In certain embodiments, Z is selected from a bridging oxide, a terminal oxide, hydroxide, sulfite, sulfate, hydrogen sulfate, thiosulfate, nitrite, nitrate, phosphite, phosphate, hydrogen phosphate, dihydrogen phosphate, carbonate, hydrogen carbonate, oxalate, cyanate, isocyanate, thiocyanate, carboxylate, sulfonate, and a combination thereof. As used herein, carboxylates can be alkylated variants (e.g., acetate), fluorinated variants (e.g., trifluoroacetate), or arylated variants (e.g., benzoates or benzoic acids). As used herein, "alkylated variants" and "arylated variants" refer to a carboxylic acid containing an alkyl group or an aryl group, respectively, as defined herein. Similarly, sulfonates can be alkylated variants (e.g., methanesulfonate) or fluorinated variants (e.g., trifluoromethanesulfonate). In certain embodiments, Z is one or more selected from trifluoroacetate, acetate, benzoate, sulfate, methanesulfonate, and trifluoromethanesulfonate. Typically, Z has an oxidation state of −4, −3, −2, or −1.

In some embodiments, $Q_aZ_b$ is a Brønsted acid, a salt, or a combination thereof. In some instances, $Q_aZ_b$ is one or more of acetic acid, ammonium acetate, lithium acetate, sodium acetate, potassium acetate, rubidium acetate, cesium acetate, francium acetate, beryllium acetate, magnesium acetate, calcium acetate, strontium acetate, barium acetate, radium acetate, benzoic acid, ammonium benzoate, lithium benzoate, sodium, potassium benzoate, rubidium benzoate, cesium benzoate, francium benzoate, beryllium benzoate, magnesium benzoate, calcium benzoate, strontium benzoate, barium benzoate, radium benzoate, trifluoroacetic acid, ammonium trifluoroacetate, lithium trifluoroacetate, sodium trifluoroacetate, potassium trifluoroacetate, trifluoroacetic acid, ammonium trifluoroacetate, lithium trifluoroacetate, sodium trifluoroacetate, potassium trifluoroacetate, rubidium trifluoroacetate, cesium trifluoroacetate, francium trifluoroacetate, beryllium trifluoroacetate, magnesium trifluoroacetate, calcium trifluoroacetate, strontium trifluoroacetate, barium trifluoroacetate, radium trifluoroacetate, sulfuric acid, ammonium sulfate, lithium sulfate, sodium sulfate, potassium sulfate, rubidium sulfate, cesium sulfate, francium sulfate, beryllium sulfate, magnesium sulfate, calcium sulfate, strontium sulfate, barium sulfate, radium sulfate, phosphoric acid, methanesulfonic acid, ammonium methanesulfonate, lithium methanesulfonate, sodium methanesulfonate, potassium methanesulfonate, rubidium methanesulfonate, cesium methanesulfonate, francium methanesulfonate, beryllium methanesulfonate, magnesium methanesulfonate, calcium methanesulfonate, strontium methanesulfonate, barium methanesulfonate, radium methanesulfonate, trifluoromethanesulfonic acid, ammonium trifluoromethanesulfonate, lithium trifluoromethanesulfonate, sodium trifluoromethanesulfonate, potassium trifluoromethanesulfonate, rubidium trifluoromethanesulfonate, cesium trifluoromethanesulfonate, francium trifluoromethanesulfonate, beryllium trifluoromethanesulfonate, magnesium trifluoromethanesulfonate, calcium trifluoromethanesulfonate, strontium trifluoromethanesulfonate, barium trifluoromethanesulfonate, or radium trifluoromethanesulfonate. In preferred embodiments, $Q_aZ_b$ is trifluoroacetic acid, acetic acid, benzoic acid, methanesulfonic acid, or a combination thereof, each of which can be substituted or unsubstituted.

In other embodiments, $Q_aZ_b$ is any suitable, non-halide containing Lewis acid, which is a strong electron pair acceptor. In embodiments where $Q_aZ_b$ is a non-halide containing Lewis acid, Q can be a cation of a transition metal, a cation of a rare-earth metal, a main group cation, or a combination thereof. In some embodiments, Q is a cation of boron, bismuth, antimony, arsenic, lanthanum, cerium, scandium, yttrium, titanium, zirconium, hafnium, silver, zinc, cadmium, aluminum, gallium, indium, germanium, tin, phosphorus, or a combination thereof. Typically, Q has an oxidation state of +5, +4, +3, +2, or +1. In certain embodiments, Q is In(III), Sc(III), Zn(II), Ti(IV), Al(III), Ga(III), B(III), Sb(III), Bi(III), or As(III). It will be understood that any one or more Q(s) can be combined with any one or more Z(s), such that fundamental chemical rules are satisfied, to form the non-halide containing Lewis acid (e.g., $Ce(OAc)_3$, $Ce(OTf)_3$, $Zn(OAc)_2$, $Zn(OTf)_2$, $ZnO$, $In(OAc)_3$, $In(OTf)_3$, $In_2O_3$, $Sb(OAc)_3$, $Sb(OTf)_3$, $Sb_2O_3$, $Bi(OAc)_3$, $Bi(OTf)_3$, $Bi_2O_3$, $Al(OTf)_3$, $Ga(OTf)_3$, $Sc(OAc)_3$, $Sc(OTf)_3$, or Sc(OMs)$_3$). As used herein, "Otf" refers to trifluoromethanesulfonate, "OMs" refers to mesylate, and "OAc" refers to acetate.

In some embodiments, the additive is water and/or ammonia.

In some embodiments, the liquid medium and/or oxidizing composition does not contain a halide ion (e.g., Cl$^-$, Br$^-$, or I$^-$). As used herein, the term "halide ion" is considered different from the term halogen atom. In particular, the term halide ion does not encompass a halogen atom (e.g., a fluorine atom, a chlorine atom, a bromine atom, or an iodine atom) attached to an aliphatic or aromatic substituent (i.e., a substituent that will not decompose to form free ions under reaction conditions). For example, iodine can be present in aromatic-iodine species, as this form of iodine would not be considered a halide ion. Instead, the term "halide ion" refers to ions of salt additives, such as alkali halide compounds (e.g., NaI, KCl, etc.). Accordingly, the halide ion can be present in the liquid medium and/or oxidizing composition in an amount less than 0.1 mol % (e.g., less than 0.05 mol %, less than 0.01 mol %, less than 0.005 mol %, less than 0.001 mol %) or about 0 mol % of the main group element.

In some embodiments, the liquid medium and/or oxidizing composition comprises a trace amount of a halide ion (e.g., Cl$^-$, Br$^-$, or I$^-$). It is possible that impurities in starting materials or from reactor corrosion can be responsible for the presence of trace halide ions. Accordingly, the halide ion can be present in an amount of about 0.00001 mol % of the main group element or more (e.g., about 0.0001 mol % or more, about 0.001 mol % or more, 0.01 mol % or more, 0.1 mol % or more, or about 1 mol % or more). Alternatively, or in addition, the halide ion can be present in an amount of about 5 mol % of the main group element or less (e.g., about 4 mol % or less, about 3 mol % or less, about 2 mol % or less, about 1 mol % or less, or about 0.1 mol % or less). Any two of the foregoing endpoints can be used to define a close-ended range, or any single endpoint can be used alone to define an open-ended range.

In some embodiments, the oxidizing composition further comprises one or more oxidizing regeneration reagents. Suitable oxidizing regeneration reagents will be readily apparent from the description set forth herein.

The invention is further illustrated by the following embodiments.

(1) A process for converting a hydrocarbon comprising at least one C—H bond to a nitrogen-functionalized product, comprising contacting the hydrocarbon and (i) an oxidizing electrophile comprising (a) a main group element or transition metal in oxidized form and (b) at least one nitrogen-containing ligand, or (ii) an oxidant and a reduced form of an oxidizing electrophile comprising (a) a main group element or transition metal and (b) at least one nitrogen-containing ligand, in a solvent to provide the nitrogen-functionalized product and an electrophile reduction product; and optionally separating the nitrogen-functionalized product and the electrophile reduction product.

(2) The process of embodiment (1), comprising separating the nitrogen-functionalized product and the electrophile reduction product.

(3) The process of embodiment (1) or embodiment (2), further comprising contacting the nitrogen-functionalized product with a compound of the formula H-Nu to form an amine, wherein Nu is a nucleophilic group that enables the formation of the amine.

(4) The process of embodiment (3), wherein Nu is oxide, hydroxide, alkoxide, aryloxide, carboxylate, thiolate, bisulfide, optionally protected amide, or optionally protected azanide.

(5) The process of embodiment (3) or embodiment (4), wherein Nu is —O, —OR$^1$, —CO$_2$R$^1$, —S, —SR$^1$, —NR$^1$, —NHR$^1$, or —NR$^1$R$^2$, in which R$^1$ and R$^2$ are the same or different and each is hydrogen, aliphatic, heteroaliphatic, aromatic, or heteroaromatic.

(6) The process of any one of embodiments (3)-(5), wherein H-Nu is NH$_3$, CH$_3$NH$_2$, PhNH$_2$, H$_2$O, CH$_3$OH, CH$_3$CH$_2$OH, or CH$_3$CO$_2$H.

(7) The process of any one of embodiments (3)-(6), wherein H-Nu is NH$_3$.

(8) The process of embodiment (1) or embodiment (2), further comprising deprotecting the nitrogen-functionalized product to form an amine.

(9) The process of any one of embodiments (3)-(8), wherein the amine comprises a monoamine, a diamine, or both a monoamine, and a diamine.

(10) The process of any one of embodiments (1)-(9), further comprising contacting the electrophile reduction product and an oxidizing regeneration reagent to regenerate the oxidizing electrophile.

(11) The process of embodiment (10), wherein the oxidizing regeneration reagent is molecular oxygen, ozone, hydrogen peroxide, organoperoxide, nitric acid, hydrazine, organohydrazine, methoxyamine, hydroxylamine, or a combination thereof.

(12) The process of any one of embodiments (1)-(11), wherein the hydrocarbon is selected from alkane, alkene, alkyne, cycloalkane, cycloalkene, heterocycloalkane, heterocycloalkene, arene, and heteroarene, each of which is optionally substituted.

(13) The process of embodiment (12), wherein the hydrocarbon is alkane, alkene, or arene.

(14) The process of any one of embodiments (1)-(13), wherein the oxidizing electrophile comprises the element mercury, thallium, lead, antimony, selenium, tellurium, bismuth, iodine, gold, platinum, palladium, silver, iridium, rhodium, osmium, or rhenium.

(15) The process of any one of embodiments (1)-(14), wherein the at least one nitrogen-containing ligand has the formula —NH$_n$Y$_{2-n}$, wherein Y is an electron withdrawing group and n is 0 or 1.

(16) The process of embodiment (15), wherein Y is aryl, —F, —COR, —C(O)OR, —C(O)NRR', —NO$_2$, —NO, —CH$_2$SO$_2$, —SO$_2$R, —SO$_2$F, —SO$_2$OH, —SO$_2$NH$_2$, or —P(O)RR', wherein R and R' are the same or different and each is aliphatic, heteroaliphatic, aromatic, or hetero aromatic.

(17) The process of embodiment (16), wherein Y is —COR, —C(O)OR, —C(O)NRR', or —SO$_2$R, wherein R and R' are the same or different and each is aliphatic, heteroaliphatic, aromatic, or heteroaromatic.

(18) The process of any one of embodiments (1)-(17), wherein the oxidizing electrophile is of the formula M$^m$(NH$_n$Y$_{2-n}$)$_p$, wherein M is a main group or transition metal cation, Y is aryl, —F, —COR, —C(O)OR, —C(O)NRR', —NO$_2$, —NO, —CH$_2$SO$_2$, —SO$_2$R, —SO$_2$F, —SO$_2$OH, —SO$_2$NH$_2$, or —P(O)RR', wherein R and R' are the same or different and each is aliphatic, heteroaliphatic, aromatic, or heteroaromatic, m is the formal oxidation state of M, n is 0 or 1, and p is 1 to m.

(19) The process of embodiment (18), wherein m is 1-8.

(20) The process of any one of embodiments (1)-(19), wherein the solvent is a non-oxidizable liquid selected from a fluorinated hydrocarbon, a sulfone, a deactivated arene, a deactivated aliphatic, a deactivated heteroarene, a deactivated heteroaliphatic, has the formula $HNY_2$ or $H_2NY$, and any combination thereof, wherein Y is aryl, —F, —COR, —C(O)OR, —C(O)NRR', —NO$_2$, —NO, —CH$_2$SO$_2$, —SO$_2$R, —SO$_2$F, —SO$_2$OH, —SO$_2$NH$_2$, or —P(O)RR', and R and R' are the same or different and each is aliphatic, heteroaliphatic, aromatic, or heteroaromatic.

(21) The process of any one of embodiments (1)-(20), wherein the reaction temperature is from 50° C. to about 300° C.

(22) An oxidizing composition comprising (a) an oxidizing electrophile comprising a main group element or transition metal in oxidized form and at least one nitrogen-containing ligand; (b) a non-oxidizable liquid selected from the group consisting of a fluorinated hydrocarbon, a sulfone, a deactivated arene, a deactivated aliphatic, a deactivated heteroarene, a deactivated heteroaliphatic, a compound of the formula $HNY_2$ or $H_2NY$, and a combination thereof, wherein Y is an electron-withdrawing group; and (c) optionally one or more additives of the formula $Z_a(NH_nY_{2-n})_p$, wherein Z is a cation, Y is aryl, —F, —COR, —C(O)OR, —C(O)NRR', —NO$_2$, —NO, —CH$_2$SO$_2$, —SO$_2$R, —SO$_2$F, —SO$_2$OH, —SO$_2$NH$_2$, or —P(O)RR', in which R and R' are the same or different and each is aliphatic, heteroaliphatic, aromatic, or heteroaromatic, a is 1 to 5, n is 0 or 1, and p is 1 to 5.

(23) The oxidizing composition of embodiment (22), wherein the oxidizing electrophile comprises the element mercury, thallium, lead, antimony, selenium, tellurium, bismuth, iodine, gold, platinum, palladium, silver, iridium, rhodium, osmium, or rhenium.

(24) The oxidizing composition of embodiment (22) or (23), wherein the at least one nitrogen-containing ligand has the formula —$NH_nY_{2-n}$, wherein Y is an electron withdrawing group and n is 0 or 1.

(25) The process of embodiment (24), wherein Y is aryl, —F, —COR, —C(O)OR, —C(O)NRR', —NO$_2$, —NO, —CH$_2$SO$_2$, —SO$_2$, —SO$_2$F, —SO$_2$NH$_2$, or —P(O)RR', wherein R and R' are the same or different and each is aliphatic, heteroaliphatic, aromatic, or hetero aromatic.

(26) The oxidizing composition of embodiment (25), wherein Y is —COR, —C(O)OR, —C(O)NRR', or —SO$_2$R, wherein R and R' are the same or different and each is aliphatic, heteroaliphatic, aromatic, or heteroaromatic.

(27) The oxidizing composition of any one of embodiments (22)-(26), wherein the oxidizing electrophile is of the formula $M^m(NH_nY_{2-n})_p$, wherein M is a main group or transition metal cation, Y is aryl, —F, —COR, —C(O)OR, —C(O)NRR', —NO$_2$, —NO, —CH$_2$SO$_2$, —SO$_2$R, ≤SO$_2$F, —SO$_2$OH, —SO$_2$NH$_2$, or —P(O)RR', wherein R and R' are the same or different and each is aliphatic, heteroaliphatic, aromatic, or heteroaromatic, m is the formal oxidation state of M, n is 0 or 1, and p is 1 to m.

(28) The oxidizing composition of embodiment (27), wherein m is 1-8.

(29) The oxidizing composition of any one of embodiments (22)-(28), wherein the composition further comprises an oxidizing regeneration reagent.

(30) The oxidizing composition of embodiment (29), wherein the oxidizing regeneration reagent is molecular oxygen, ozone, hydrogen peroxide, organoperoxide, nitric acid, hydrazine, organohydrazine, methoxyamine, hydroxylamine, or a combination thereof.

(31) The oxidizing composition of any one of embodiments (22)-(30), wherein at least one additive of the formula $Z_a(NH_nY_{2-n})_p$ is present.

The following examples further illustrate the invention but, of course, should not be construed as in any way limiting its scope.

EXAMPLES

For quantifying substrate and product concentrations in solution by nuclear magnetic resonance (NMR), the reaction mixture was dissolved in approximately 0.5 mL trifluoroacetic acid ("HOTFA"). Typically 0.1 mmol of an appropriate standard (e.g., 1,1,2,2-tetrachloroethane ("1,1,2,2-TCE")) was added to the mixture as an internal standard. An aliquot of this mixture was then pipetted into a 5 mm NMR tube, the tube was capped with a standard NMR cap containing a ~2 mm hole, and then a 2 mm capillary containing deuterated solvent (e.g., d$_6$-benzene, d$_6$-acetone, d$_6$-dimethyl sulfoxide, etc.) was placed into the tube through the hole. NMR spectra ($^1$H or $^{19}$F) were then taken with >a 10 second relaxation delay (with no decoupling).

The following examples demonstrates the oxidation of various hydrocarbons in the presence of an oxidizing electrophile comprising a main group element or transition metal in an embodiment of the invention. The results of various experiments are set forth in Table 1.

TABLE 1

| Entry | Oxidant | Acid | Substrate | Temp. (° C.) | Time (h) | Products (% yield) |
|---|---|---|---|---|---|---|
| 1 | Tl(OTFA)$_3$ | HNTf$_2$ | Me—H | 180 | 3 | MeNTf$_2$ (50%), MeOTFA (4%) |
| 2 | Tl(OTFA)$_3$ | HNTf$_2$ | Et—H | 80 | 1 | EtNTf$_2$ (14%), C$_2$H$_4$(NTf$_2$)$_2$ (17%), EG(OTFA)$_2$ (2%), Tf$_2$NCH$_2$CH$_2$OTFA (5%), EtOTFA (20%) |
| 3 | Tl(OTFA)$_3$ | HNTf$_2$ | C$_2$H$_4$ | 80 | 1 | EG(OTFA)$_2$ (3%), C$_2$H$_4$(NTf$_2$)$_2$ (9.4%), Tf$_2$NCH$_2$CH$_2$OTFA (4%) |
| 4 | Hg(NTf$_2$)$_2$ | HNTf$_2$ | Me—H | 180 | 3 | MeNTf$_2$ (3.5%), MeHgNTf (5%) |
| 5 | Hg(NTf$_2$)$_2$ | HNTf$_2$ | Et—H | 180 | 3 | EtNTf$_2$ (10%) |
| 6 | Hg(N(SO$_2$F)$_2$)$_2$ | HN(SO$_2$F)$_2$ | Me—H | 180 | 3 | MeN(SO$_2$F)$_2$ (45%), MeHgN(SO$_2$F)$_2$ (3%) |
| 7 | Hg(N(SO$_2$F)$_2$)$_2$ | HN(SO$_2$F)$_2$ | Et—H | 180 | 3 | EtN(SO$_2$F)$_2$ (60%) |
| 8 | $^F$PhI(OTFA)$_2$ | HNTf$_2$ | Et—H | 150 | 2 | EtNTf$_2$ (31%), C$_2$H$_4$(NTf$_2$)$_2$ (33%), EtOTFA (14%) |
| 9 | $^F$PhI(OTFA)$_2$ | HNTf$_2$ | C$_2$H$_4$ | 80 | 1 | C$_2$H$_4$(NTf$_2$)$_2$ (15%) |
| 10 | p-NO$_2$—PhI(OTFA)$_2$ | HNTf$_2$ | Et—H | 150 | 2 | EtNTf$_2$ (36%), C$_2$H$_4$(NTf$_2$)$_2$ (21%), EtOTFA (4%) |

TABLE 1-continued

| Entry | Oxidant | Acid | Substrate | Temp. (° C.) | Time (h) | Products (% yield) |
|---|---|---|---|---|---|---|
| 11 | $^F$PhI(NTf$_2$)$_2$ | HNTf$_2$ | Ph—H | 100 | 1 | PhNTf$_2$ (7%), $^F$PhI(Ph)(NTf$_2$) (93%) |
| 12 | $^F$PhI(NTf$_2$)$_2$ | HNTf$_2$ | Me—H | 100 | 2 | MeNTf$_2$ (40%) |
| 13 | $^F$PhI(NTf$_2$)$_2$ | HNTf$_2$ | Et—H | 100 | 2 | EtNTf$_2$ (33%), C$_2$H$_4$(NTf$_2$)$_2$ (50%) |
| 14 | Sb(OMe)$_5$ | HNTf$_2$ | C$_2$H$_4$ | 60 | 3 | Tf$_2$NCH$_2$CH$_2$OH (7%) |

TFA: trifluoroacetate
Tf: trifluoromethylsulfonyl
EG: ethylene glycol
$^F$Ph: perfluorophenyl Example 1

This example demonstrates the oxidation of ethane in the presence of oxidizing electrophile mercury di[bis(trifluoromethylsulfonyl)imide] ("Hg(NTf$_2$)$_2$").

Figure 3:
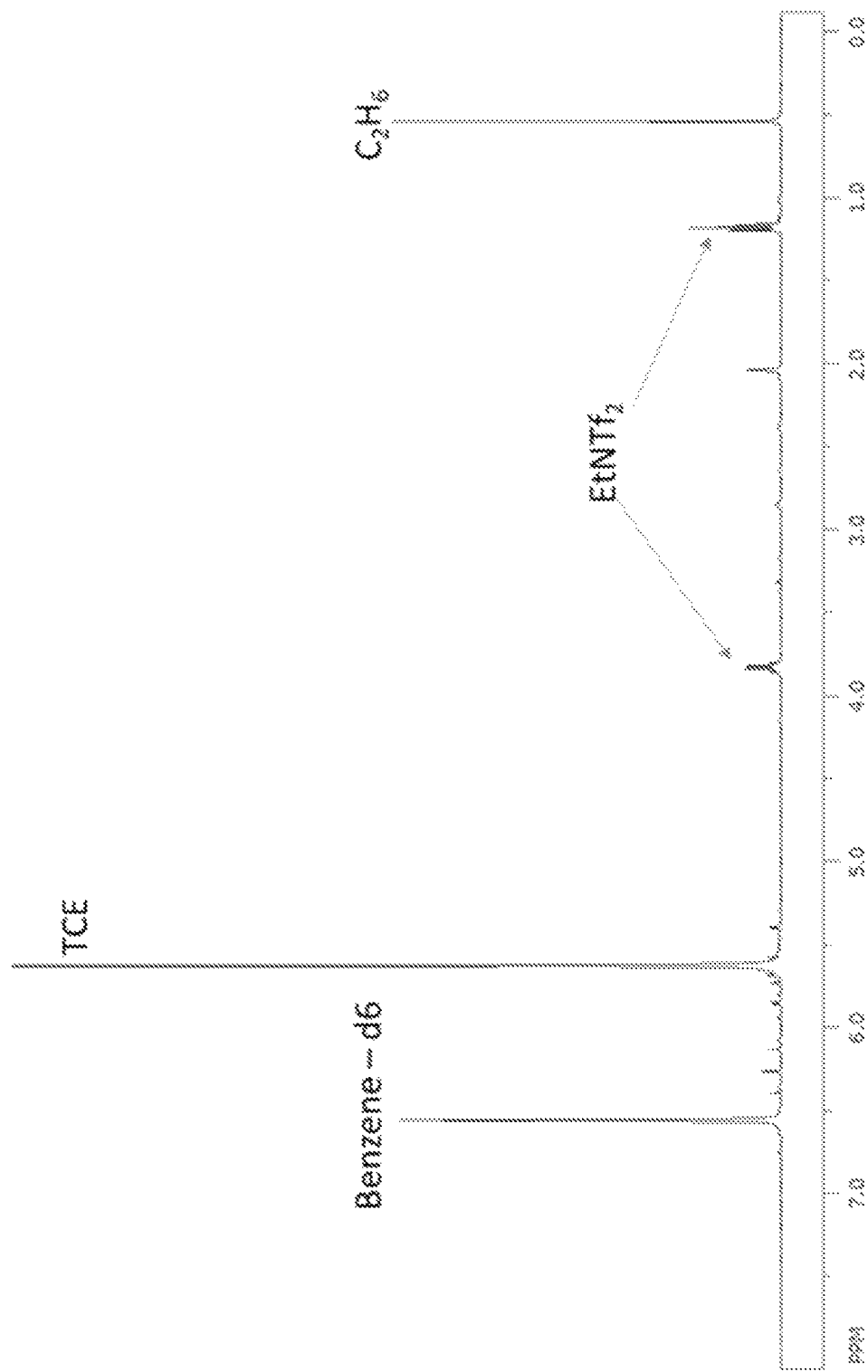
FIG. 3 illustrates the $^1H$ NMR spectrum of the crude reaction mixture from the reaction of $Hg(NTf_2)_2$ in $HNTf_2$ with ethane.

A 2 mL glass vial, equipped with a PTFE-coated magnetic stir bar, was charged with 0.1 mmol) of Hg(NTf$_2$)$_2$ in a glove box. To the vial was added approximately 500 mg HNTf$_2$. The vial was inserted into a stainless steel, high pressure reactor and sealed. With the inlet valve of the reactor open, it was pressure degas sed with argon, 5 times at 500 psig (about 35 kg/cm$^2$), followed by ethane, 5 times at 500 psig (about 35 kg/cm$^2$). The reactor was then charged with 500 psig (about 35 kg/cm$^2$) ethane and the inlet valve was shut. The reactor was heated to 180° C. with stirring at 1000 rpm for 3 hours. The reactor was cooled to room temperature, and the pressure was slowly released. The contents of the vial insert were dissolved in approximately 0.5 mL HOTFA, and 0.1 mmol 1,1,2,2-TCE was added as an internal standard. The formation of products was determined by $^1$H NMR of the reaction mixture using a benzene-d$_6$ coaxial for locking and shimming with the 1,1,2,2-TCE calibrated at 5.63 ppm. See FIG. 3 for an exemplary $^1$H NMR spectrum.

The total yield of EtNTf$_2$, based on Hg(II) added, was approximately 10% (Table 1, Entry 5). As is apparent from the results set forth in Table 1, oxidation with Hg(NTf$_2$)$_2$ results in mono-functionalized EtNTf$_2$ as the sole product detected.

Example 2

This example demonstrates the oxidation of ethane in the presence of oxidizing electrophile mercury bis(fluorosulphuryl)imide ("Hg(N(SO$_2$F)$_2$)$_2$").

A 2 mL glass vial, equipped with a polytetrafluoroethylene (PTFE)-coated magnetic stir bar, was charged with 56 mg (0.1 mmol) of Hg(N(SO$_2$F)$_2$)$_2$ in a glove box. To the vial was added approximately 0.3 mL (3.14 mmol) of HN(SO$_2$F)$_2$. The vial was inserted into a stainless steel, high pressure reactor and sealed. With the inlet valve of the reactor open, it was pressure degassed with argon, 5 times at 500 psig (about 35 kg/cm$^2$), followed by ethane, 5 times at 500 psig (about 35 kg/cm$^2$). The reactor was then charged with 500 psig (about 35 kg/cm$^2$) ethane, and the inlet valve was shut. The reactor was heated to 180° C. with stirring at 1000 rpm for 3 hours. The reactor was cooled to room temperature and the pressure was slowly released. The contents of the vial insert were dissolved in approximately 0.5 mL HOTFA and 0.1 mmol 1,1,2,2-TCE was added as an internal standard. The formation of products was determined by $^1$H NMR of the reaction mixture using a benzene-d$_6$ coaxial for locking and shimming with the 1,1,2,2-TCE calibrated at 5.63 ppm.

The total yield of EtN(SO$_2$F)$_2$, based on Hg(II) added, was 60% (Table 1, Entry 7). As is apparent from the results set forth in Table 1, oxidation with Hg(N(SO$_2$F)$_2$)$_2$ results in mono-functionalized EtN(SO$_2$F)$_2$.

Example 3

This example demonstrates the oxidation of ethane in the presence of oxidizing electrophile thallium di[bis(trifluoromethylsulfonyl)imide] ("Tl(NTf$_2$)$_2$"), generated in situ from thallium trifluoroacetate ("Tl(OTFA)$_3$").

Figure 4:
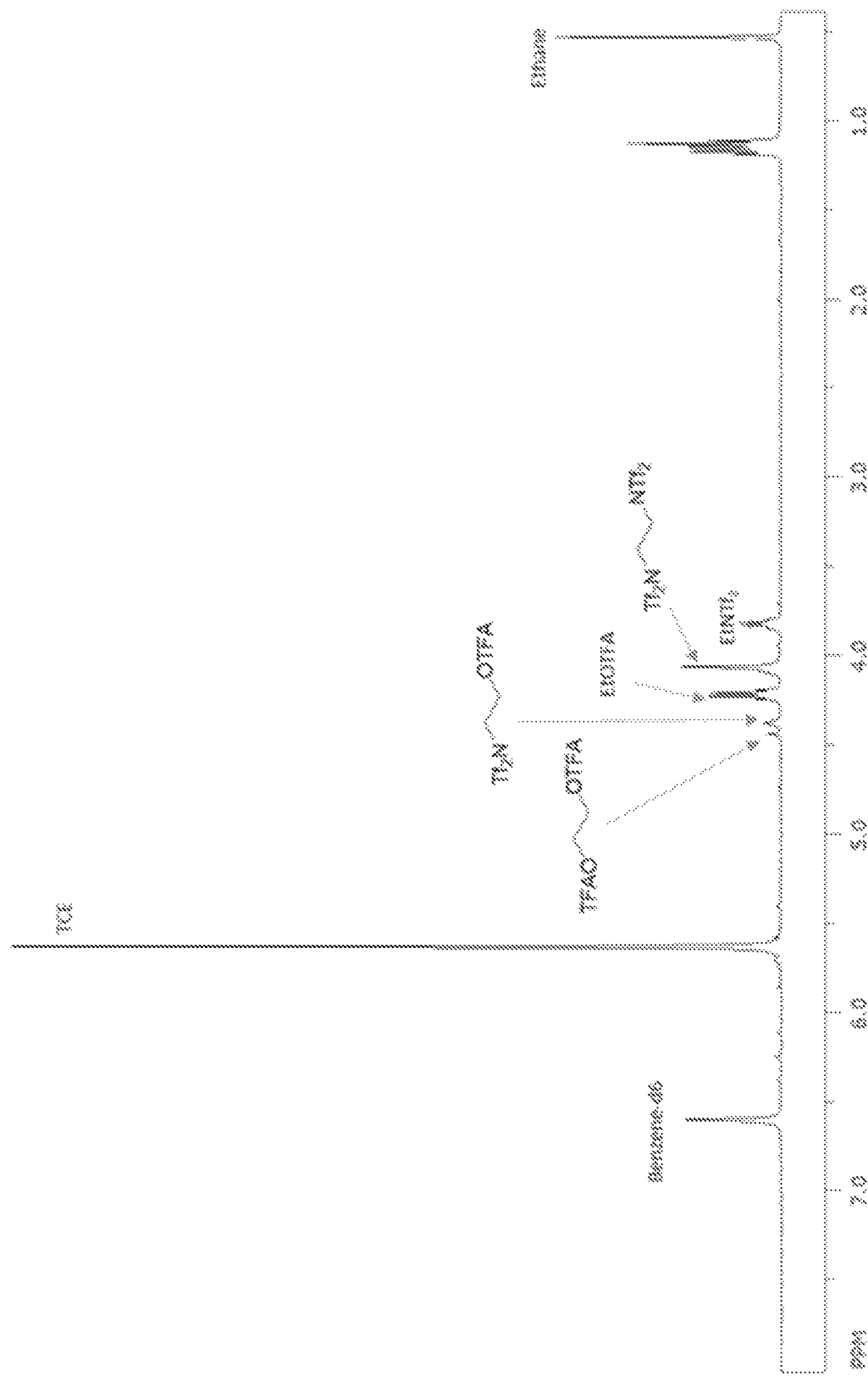
FIG. 4 illustrates the $^1H$ NMR spectrum of the crude reaction mixture from the reaction of $Tl(OTFA)_3$ in $HNTf_2$ with ethane.

A 2 mL glass vial, equipped with a PTFE-coated magnetic stir bar, was charged with 55 mg (0.1 mmol) of Tl(OTFA)$_3$ in a glove box. To the vial was added approximately 600 mg (about 2.13 mmol) of HNTf$_2$. The vial was inserted into a stainless steel, high pressure reactor and sealed. With the inlet valve of the reactor open, it was pressure degassed with argon, 5 times at 500 psig (about 35 kg/cm$^2$), followed by ethane, 5 times at 500 psig (about 35 kg/cm$^2$). The reactor was then charged with 500 psig (about 35 kg/cm$^2$) ethane and the inlet valve was shut. The reactor was heated to 80° C. with stirring at 1000 rpm for 1 hour. The reactor was cooled to room temperature, and the pressure was slowly released. The contents of the vial insert were dissolved in approximately 0.5 mL HOTFA and 0.1 mmol 1,1,2,2-TCE was added as an internal standard. The formation of products was determined by $^1$H NMR of the reaction mixture using a benzene-d$_6$ coaxial for locking and shimming with the 1,1,2,2-TCE calibrated at 5.63 ppm. See FIG. 4 for an exemplary $^1$H NMR spectrum.

Figure 5:
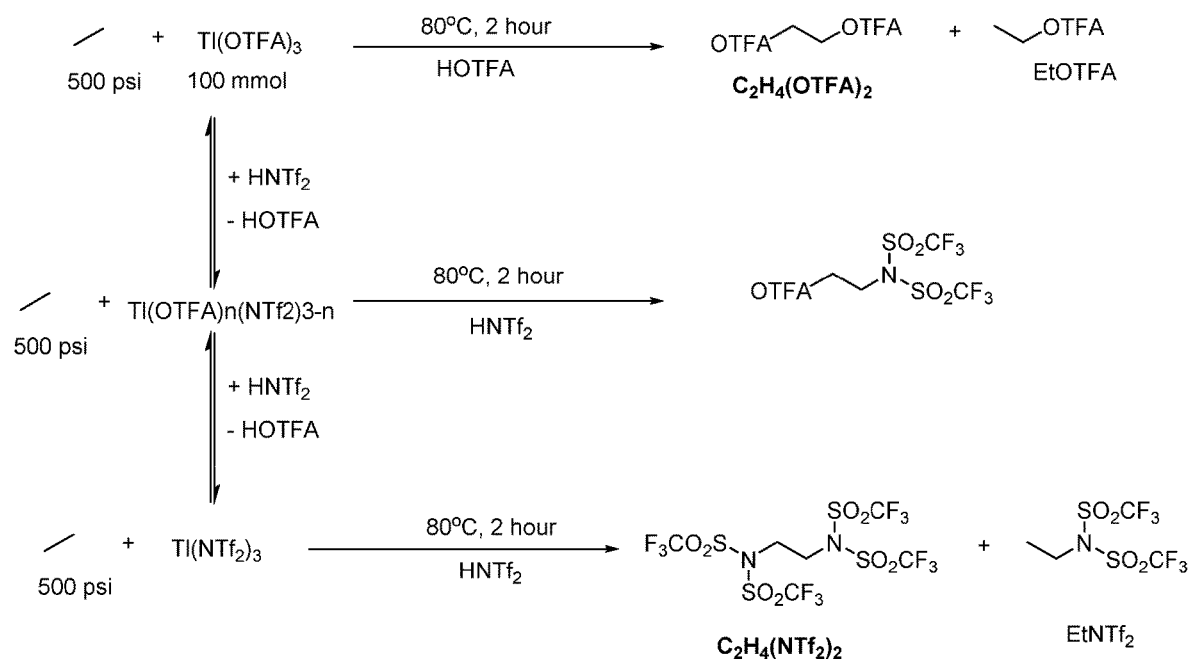
FIG. 5 illustrates the proposed reaction progression diagram for the reaction of Example 3.
Figure 6:
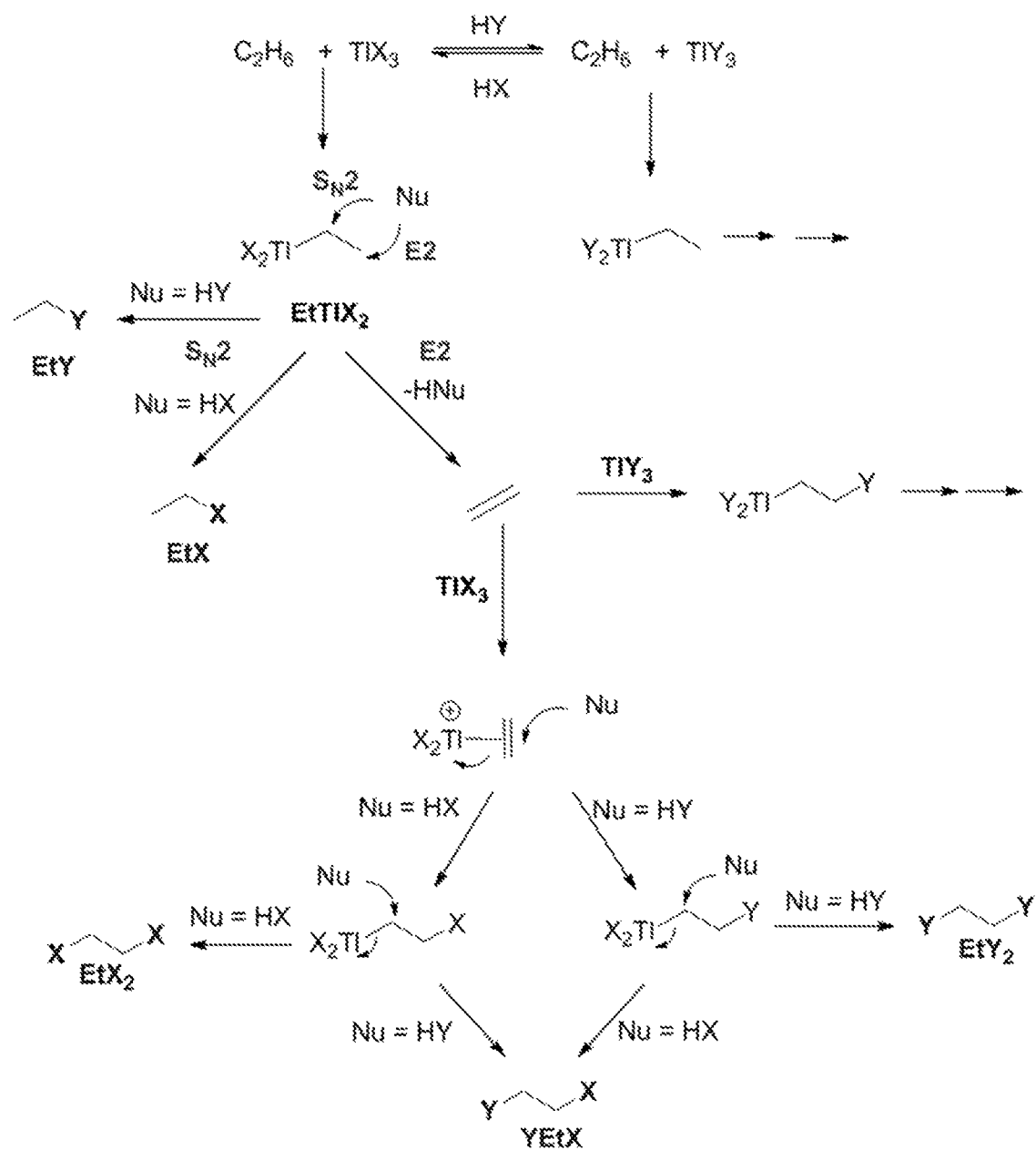
FIG. 6 illustrates the proposed mechanistic diagram of the reaction of Example 3.

The total yield of all products (i.e., EtNTf$_2$, C$_2$H$_4$(NTf$_2$)$_2$, EtOTFA, C$_2$H$_4$(OTFA)$_2$, C$_2$H$_4$(OTFA)(NTf$_2$)) based on Tl(OTFA)$_3$ added, was 63%. In addition, the product distribution results are set forth in Table 1, Entry 2. As is apparent from the results set forth in the $^1$H NMR spectrum and Table 1, mono-functionalized EtNTf$_2$ and the ethylene diamine derivative, C$_2$H$_4$(NTf$_2$)$_2$, as well as the analogous OTFA products (from use of Tl(OTFA)$_3$), and the mixed O—N functionalized product, TFAO—CH$_2$CH$_2$NTf$_2$ were produced. The selective mixture of products, as a result of the mixed anion Tl$^{III}$ species, provides strong evidence that the reaction is proceeding through a C—H activation mechanism, as demonstrated by the proposed reaction progression diagram at FIG. 5 and the proposed mechanistic diagram at FIG. 6.

Example 4

This example demonstrates the oxidation of ethane in the presence of oxidizing electrophile C$_6$F$_5$I(NTf$_2$)$_2$, generated in situ from C$_6$F$_5$I(OTFA)$_2$.

A 2 mL glass vial, equipped with a PTFE-coated magnetic stir bar, was charged with 52 mg (0.1 mmol) of C$_6$F$_5$I(OTFA)$_2$ in a glove box. To the vial was added approximately 600 mg (about 2.13 mmol) of HNTf$_2$. The vial was inserted into a stainless steel, high pressure reactor and sealed. With the inlet valve of the reactor open, it was pressure degassed with argon, 5 times at 500 psig (about 35 kg/cm$^2$), followed by ethane, 5 times at 500 psig (about 35 kg/cm$^2$). The reactor was then charged with 500 psig (about 35 kg/cm$^2$) ethane, and the inlet valve was shut. The reactor was heated to 130° C. with stirring at 1000 rpm for 2 hours. The reactor was cooled to room temperature, and the pressure was slowly released. The contents of the vial insert were dissolved in approximately 0.5 mL HOTFA and 0.1 mmol 1,1,2,2-TCE was added as an internal standard. The formation of products was determined by $^1$H NMR of the reaction mixture using a benzene-d$_6$ coaxial for locking and shimming with the 1,1,2,2-TCE calibrated at 5.63 ppm.

The total yield of all products (i.e., EtNTf$_2$, C$_2$H$_4$(NTf$_2$)$_2$, EtOTFA, C$_2$H$_4$(OTFA)$_2$, C$_2$H$_4$(OTFA)(NTf$_2$)), based on C$_6$F$_5$I(OTFA)$_2$, added, was 78%. In addition, the product distribution results are set forth in Table 1, Entry 8. As is apparent from the results set forth in the $^1$H NMR spectrum and Table 1, mono-functionalized EtNTf$_2$ and the ethylene diamine derivative, C$_2$H$_4$(NTf$_2$)$_2$, as well as the analogous OTFA products (from use of C$_6$F$_5$I(OTFA)$_2$), and the mixed O—N functionalized product, TFAO—CH$_2$CH$_2$NTf$_2$ were produced. The selective mixture of products, as a result of the mixed anion C$_6$F$_5$I(Y)$_2$ species, provides strong evidence that the reaction is proceeding through a C—H activation mechanism (see, for example, FIGS. 5 and 6).

Example 5

This example demonstrates the oxidation of ethane in the presence of oxidizing electrophile C$_6$F$_5$I(NTf$_2$)$_2$, synthesized from C$_6$F$_5$I(OTFA)$_2$ via exchange with HNTf$_2$ in chloroform.

A 2 mL glass vial, equipped with a PTFE-coated magnetic stir bar, was charged with 30 mg (0.035 mmol) of C$_6$F$_5$I (NTf$_2$)$_2$ in a glove box. To the vial was added approximately 500 mg (about 2.13 mmol) of HNTf$_2$. The vial was inserted into a stainless steel, high pressure reactor and sealed. With the inlet valve of the reactor open, it was pressure degassed with argon, 5 times at 500 psig (about 35 kg/cm$^2$), followed by ethane, 5 times at 500 psig (about 35 kg/cm$^2$). The reactor was then charged with 500 psig (about 35 kg/cm$^2$) ethane, and the inlet valve was shut. The reactor was heated to 100° C. with stirring at 1000 rpm for 2 hours. The reactor was cooled to room temperature, and the pressure was slowly released. The contents of the vial insert were dissolved in approximately 0.5 mL HOTFA and 0.01 mmol 1,1,2,2-TCE was added as an internal standard. The formation of products was determined by $^1$H NMR of the reaction mixture using a benzene-d$_6$ coaxial for locking and shimming with the 1,1,2,2-TCE calibrated at 5.63 ppm.

The total yield of all products (i.e., EtNTf$_2$ and EDA (NTf$_2$)$_2$), based on C$_6$F$_5$I(NTf$_2$)$_2$, added, was 83%. In addition, the product distribution results are set forth in Table 1, Entry 13. As is apparent from the results set forth in Table 1, mono-functionalized EtNTf$_2$ and the ethylene diamine derivative, C$_2$H$_4$(NTf$_2$)$_2$, were produced.

Example 6

This example demonstrates the oxidation of methane in the presence of oxidizing electrophile mercury di[bis(trifluoromethylsulfonyl)imide] ("Hg(NTf$_2$)$_2$").

A 2 mL glass vial, equipped with a PTFE-coated magnetic stir bar, was charged with 0.1 mmol of Hg(NTf$_2$)$_2$ in a glove box. To the vial was added approximately 500 mg HNTf$_2$. The vial was inserted into a stainless steel, high pressure reactor and sealed. With the inlet valve of the reactor open, it was pressure degas sed with argon, 5 times at 500 psig (about 35 kg/cm$^2$), followed by methane, 5 times at 500 psig (about 35 kg/cm$^2$). The reactor was then charged with 500 psig (about 35 kg/cm$^2$) methane, and the inlet valve was shut. The reactor was heated to 180° C. with stirring at 1000 rpm for 3 hours. The reactor was cooled to room temperature, and the pressure was slowly released. The contents of the vial insert were dissolved in approximately 0.5 mL dimethyl sulfoxide-d$_6$ and 0.1 mmol 1,1,2,2-TCE was added as an internal standard. The formation of products was determined by $^1$H NMR of the reaction mixture with the 1,1,2,2-TCE calibrated at 5.63 ppm. See FIG. 7 for an exemplary $^1$H NMR spectrum.

Figure 7:
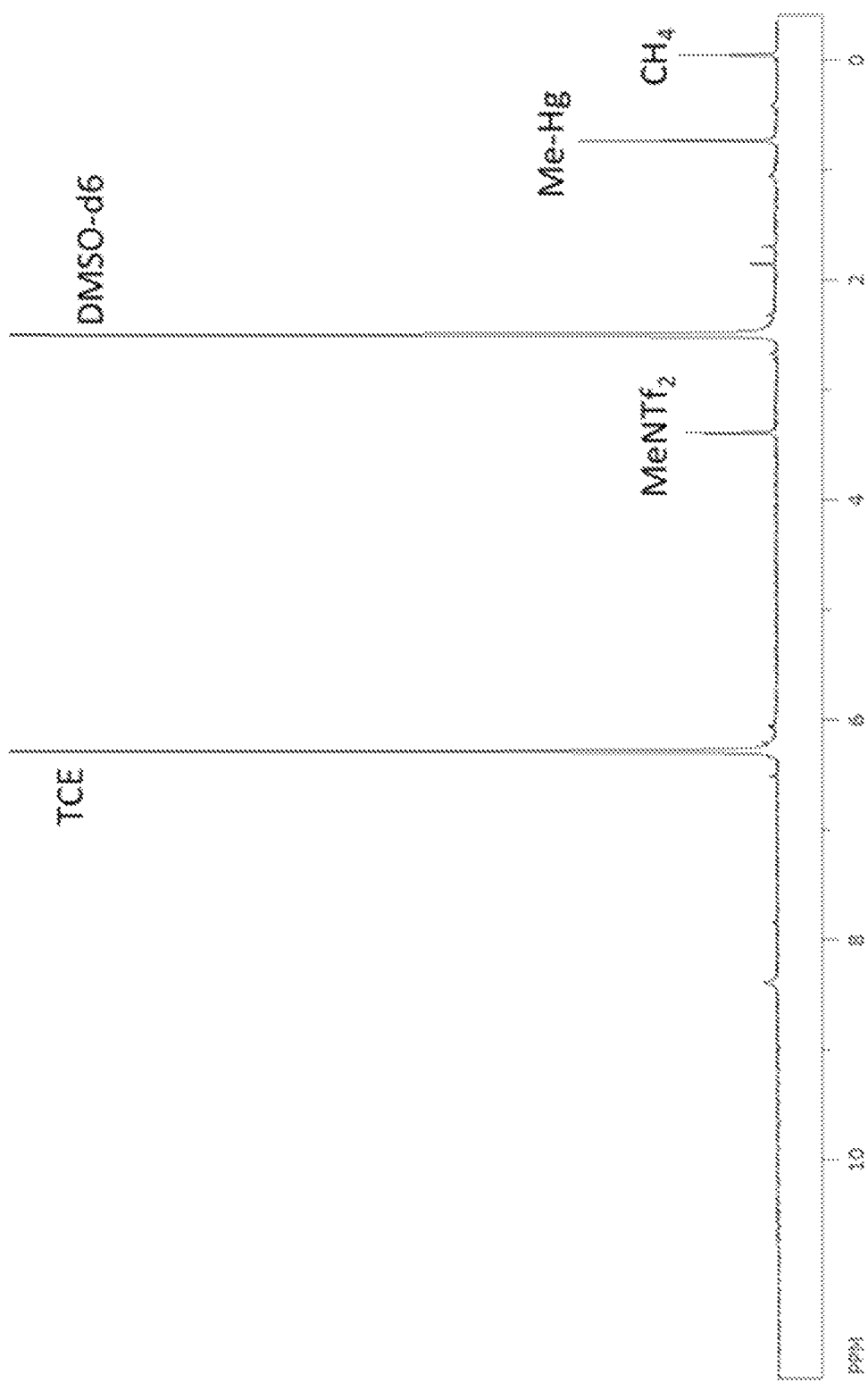
FIG. 7 illustrates the $^1H$ NMR spectrum of the crude reaction mixture from the reaction of $Hg(NTf_2)_2$ with methane in $HNTf_2$.

As is apparent from FIG. 7 and the results set forth in Table 1, Entry 4, the oxidation of methane generates both CH$_3$HgNTf$_2$ and CH$_3$NTf$_2$, which were confirmed through independent syntheses of these materials. Using the independently produced CH$_3$HgNTf$_2$, it was shown that CH$_3$HgNTf$_2$ in HNTF$_2$ at 180° C. slowly generates CH$_3$NTf$_2$ as the only functionalized product detected. The slow rate of functionalization (about 20% after one hour at 180° C.) is consistent with the observation of MeHg(NTf$_2$) in the post reaction mixtures of Hg(NTf$_2$)$_2$ with methane.

In addition, the reaction of independently synthesized EtHgNTf$_2$ was investigated in HNTf$_2$ at 180° C. for 1 h. The reaction rapidly and quantitatively generated EtNTf$_2$, and no unreacted EtHgNTf$_2$ nor Tf$_2$NCH$_2$CH$_2$NTf$_2$ were observed. The observation that the reaction of EtHgNTf$_2$ to generate EtNTf$_2$ was much faster than that of CH$_3$HgNTf$_2$ to generate CH$_3$NTf$_2$ is consistent with the lack of observation of EtHgNTf$_2$ as an intermediate in the reaction of ethane with Hg(NTf$_2$)$_2$. In addition, the lack of Tf$_2$NCH$_2$CH$_2$NTf$_2$ from the reaction of EtHgNTf$_2$ is consistent with the observation that only EtNTf$_2$ is generated in the reaction of ethane with Hg(NTf$_2$)$_2$.

Example 7

This example demonstrates the oxidation of methane in the presence of oxidizing electrophile mercury di[bis(fluorosulfonyl)imide] ("Hg(N(SO$_2$F)$_2$)$_2$").

A 2 mL glass vial, equipped with a PTFE-coated magnetic stir bar, was charged with 0.1 mmol of Hg(N(SO$_2$F)$_2$)$_2$ in a glove box. To the vial was added approximately 0.3 mL HN(SO$_2$F)$_2$. The vial was inserted into a stainless steel, high pressure reactor and sealed. With the inlet valve of the reactor open, it was pressure degassed with argon, 5 times at 500 psig (about 35 kg/cm$^2$), followed by methane, 5 times at 500 psig (about 35 kg/cm$^2$). The reactor was then charged with 500 psig (about 35 kg/cm$^2$) methane, and the inlet valve was shut. The reactor was heated to 180° C. with stirring at 1000 rpm for 3 hours. The reactor was cooled to room temperature, and the pressure was slowly released. The contents of the vial insert were dissolved in approximately 0.5 mL HOTFA and 0.1 mmol 1,1,2,2-TCE was added as an internal standard. The formation of products was determined by $^1$H NMR of the reaction mixture using a benzene-d$_6$ coaxial for locking and shimming with the 1,1,2,2-TCE calibrated at 5.63 ppm.

The total combined yield of MeN(SO$_2$F)$_2$ and MeHgN (SO$_2$F)$_2$ observed in the post reaction mixture was 48% based on added Hg(II). The selectivity of the two products as well as the total yield is set forth in Table 1, Entry 6.

Example 8

This example demonstrates the oxidation of methane in the presence of oxidizing electrophile thallium di[bis(trifluoromethylsulfonyl)imide] ("Tl(NTf$_2$)$_2$"), generated in situ from thallium trifluoroacetate ("T1(OTFA)$_3$").

A 2 mL glass vial, equipped with a PTFE-coated magnetic stir bar, was charged with 55 mg (0.1 mmol) of T1(OTFA)$_3$ in a glove box. To the vial was added approximately 600 mg (about 2.13 mmol) of HNTf$_2$. The vial was inserted into a stainless steel, high pressure reactor and sealed. With the inlet valve of the reactor open, it was pressure degassed with argon, 5 times at 500 psig (about 35 kg/cm$^2$), followed by methane, 5 times at 500 psig (about 35 kg/cm$^2$). The reactor was then charged with 500 psig (about 35 kg/cm$^2$) methane and the inlet valve was shut. The reactor was heated to 180° C. with stirring at 1000 rpm for 3 hours. The reactor was cooled to room temperature, and the pressure was slowly released. The contents of the vial insert were dissolved in approximately 0.5 mL HOTFA and 0.1 mmol 1,1,2,2-TCE was added as an internal standard. The formation of products was determined by $^1$H NMR of the reaction mixture using a benzene-d$_6$ coaxial for locking and shimming with the 1,1,2,2-TCE calibrated at 5.63 ppm.

The total yield of MeNTf$_2$ and MeOTFA observed in the post reaction mixture was 54% based on added Tl(III). The selectivity of the two products as well as the total overall yields are set forth in Table 1, Entry 1.

Example 9

This example demonstrates the oxidation of methane in the presence of oxidizing electrophile C$_6$F$_5$I(NTf$_2$)$_2$, synthesized from C$_6$F$_5$I(OTFA)$_2$ via exchange with HNTf$_2$ in chloroform.

A 2 mL glass vial, equipped with a PTFE-coated magnetic stir bar, was charged with 30 mg (0.035 mmol) of C$_6$F$_5$I (NTf$_2$)$_2$ in a glove box. To the vial was added approximately 500 mg (about 2.13 mmol) of HNTf$_2$. The vial was inserted into a stainless steel, high pressure reactor and sealed. With the inlet valve of the reactor open, it was pressure degassed with argon, 5 times at 500 psig (about 35 kg/cm$^2$), followed by methane, 5 times at 500 psig (about 35 kg/cm$^2$). The reactor was then charged with 500 psig (about 35 kg/cm$^2$) methane, and the inlet valve was shut. The reactor was heated to 100° C. with stirring at 1000 rpm for 2 hours. The reactor was cooled to room temperature, and the pressure was slowly released. The contents of the vial insert were dissolved in approximately 0.5 mL HOTFA and 0.01 mmol 1,1,2,2-TCE was added as an internal standard. The formation of products was determined by $^1$H NMR of the reaction mixture using a benzene-d$_6$ coaxial for locking and shimming with the 1,1,2,2-TCE calibrated at 5.63 ppm.

The total yield of all products (i.e., MeNTf$_2$), based on C$_6$F$_5$I(NTf$_2$)$_2$, added, was 40%. In addition, the product distribution results are set forth in Table 1, Entry 12. As is apparent from the results set forth in Table 1, mono-functionalized MeNTf$_2$ was the only product produced.

Example 10

This example demonstrates the oxidation of ethylene in the presence of oxidizing electrophile thallium di[bis(trifluoromethylsulfonyl)imide] ("Tl(NTf$_2$)$_2$"), generated in situ from thallium trifluoroacetate ("Tl(OTFA)$_3$").

Figure 8:
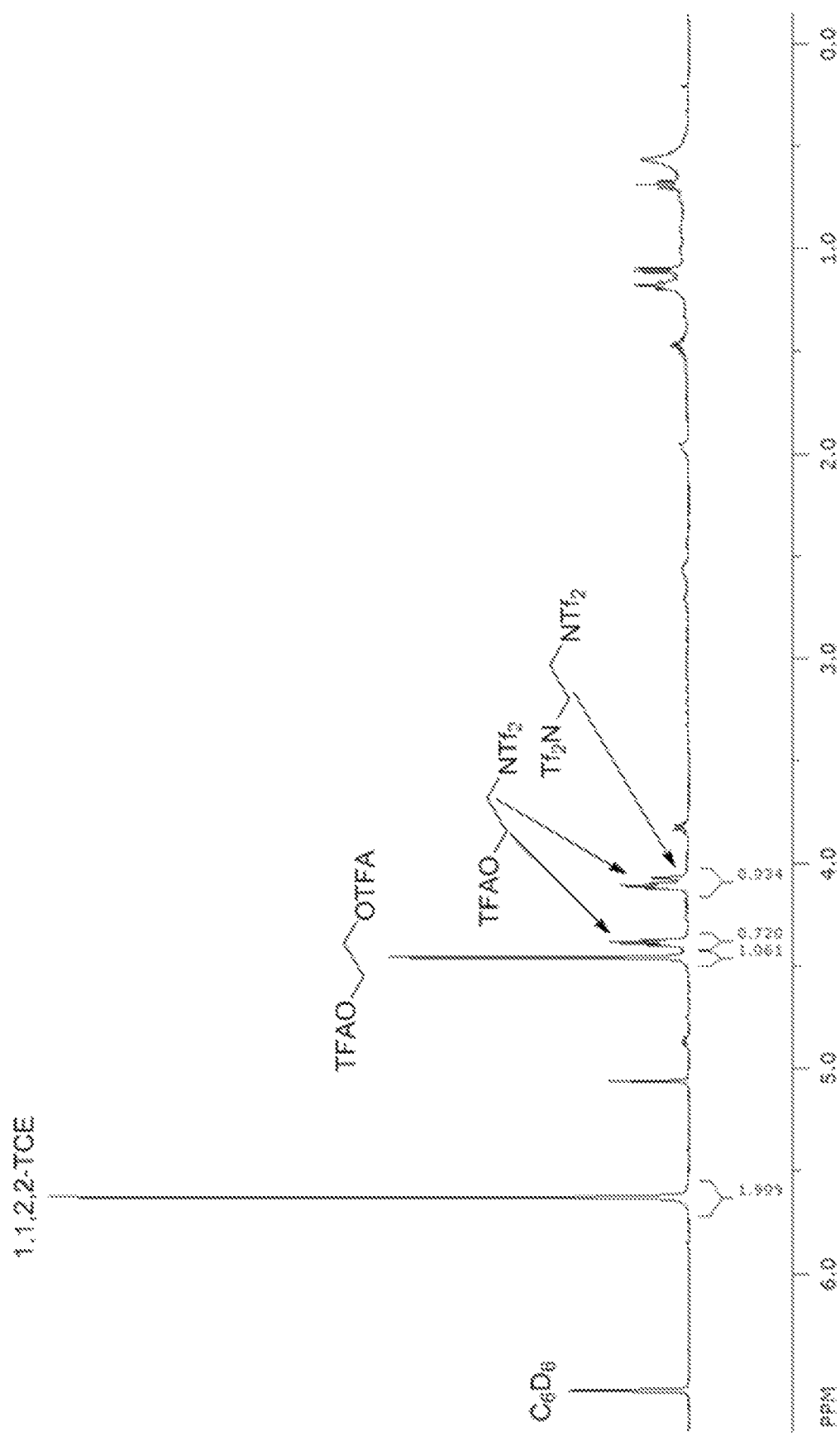
FIG. 8 illustrates the $^1H$ NMR spectrum of the crude reaction mixture from the reaction of $Tl(OTFA)_3$ with ethylene in a solvent mixture of $HNTf_2$ and $HN(TFA)_2$.

A 2 mL glass vial, equipped with a PTFE-coated magnetic stir bar, was charged with 0.1 mmol of Tl(OTFA)$_3$. To the vial was added approximately 500 mg (about 1.8 mmol) of HNTf$_2$ and 500 mg (about 2.4 mmol) of HN(TFA)$_2$. The vial was hand tightened under argon and quickly sealed. With the inlet valve of the vial open, it was pressure degassed with argon, 5 times at 500 psig (about 35 kg/cm$^2$). The vial was subsequently charged with 200 psig (about 7 kg/cm$^2$) of a lecture bottle containing 8 psig of ethylene and 492 psig of argon, and the inlet valve was shut. The reactor was heated to 70° C. with stirring at 1000 rpm for 1 hour. The reactor was cooled to room temperature, and the pressure was slowly released. The contents of the vial insert were dissolved in approximately 0.5 mL HOTFA, and 0.1 mmol 1,1,2,2-TCE was added as an internal standard. The formation of products was determined by $^1$H NMR of the reaction mixture using a benzene-d$_6$ coaxial for locking and shimming with the 1,1,2,2-TCE calibrated at 5.63 ppm. See FIG. 8 for an exemplary $^1$H NMR spectrum.

The total yield of all products (i.e., C$_2$H$_4$(NTf$_2$)$_2$, C$_2$H$_4$ (OTFA)$_2$ and C$_2$H$_4$(OTFA)(NTf$_2$)), based on Tl(OTFA)$_3$, added, was 16% (which corresponds to complete consumption of ethylene in the reactor). As is apparent from the results set forth in FIG. 8, the oxidation of ethylene does not form EtNTf$_2$ and the analogous OTFA products (from use of Tl(OTFA)$_3$) when the concentration of ethylene is sufficiently low. However the di-functionalized ethylene diamine derivative, C$_2$H$_4$(NTf$_2$)$_2$, as well as the analogous OTFA product, and the mixed O—N functionalized product, TFAO—CH$_2$CH$_2$NTf$_2$ were readily apparent. The results are summarized in Table 1, entry 3.

Example 11

This example demonstrates the oxidation of ethylene in the presence of oxidizing electrophile pentafluorophenyl-iodo-di[bis(trifluoromethylsulfonyl)imide] ("$^F$PhI(NTf$_2$)$_2$"), generated in situ from pentafluorophenyl bis(trifluoroacetoxy)iodobenzene ("$^F$PhI(OTFA)$_2$").

A 2 mL glass vial, equipped with a PTFE-coated magnetic stir bar, was charged with 0.1 mmol of $^F$PhI(OTFA)$_2$. To the vial was added approximately 500 mg (about 1.8 mmol) of HNTf$_2$. The vial was hand tightened under argon and quickly sealed. With the inlet valve of the vial open, it was pressure degas sed with argon, 5 times at 500 psig (about 35 kg/cm$^2$). The vial was subsequently charged with 200 psig (about 7 kg/cm$^2$) of a lecture bottle containing 8 psig of ethylene and 492 psig of argon, and the inlet valve was shut. The reactor was heated to 70° C. with stirring at 1000 rpm for 1 hour. The reactor was cooled to room temperature, and the pressure was slowly released. The contents of the vial insert were dissolved in approximately 0.5 mL HOTFA, and 0.1 mmol 1,1,2,2-TCE was added as an internal standard. The formation of products was determined by $^1$H NMR of the reaction mixture using a benzene-d$_6$ coaxial for locking and shimming with the 1,1,2,2-TCE calibrated at 5.63 ppm.

The only observed product was C$_2$H$_4$(NTf$_2$, and it was formed in a yield of 15% based on added $^F$PhI(OTFA)$_2$ (which corresponds to complete consumption of ethylene in the reactor). The oxidation of ethylene does not form EtNTf$_2$ and the analogous OTFA products (from use of $^F$PhI (OTFA)$_2$) when the concentration of ethylene is sufficiently low. However the di-functionalized ethylene diamine derivative, C$_2$H$_4$(NTf$_2$)$_2$ was readily apparent. The results are summarized in Table 1, entry 9.

Example 12

This example demonstrates the oxidation of benzene in the presence of oxidizing electrophile C$_6$F$_5$I(NTf$_2$)$_2$, synthesized from C$_6$F$_5$I(OTFA)$_2$ via exchange with HNTf$_2$ in chloroform.

A 2 mL glass vial, equipped with a PTFE-coated magnetic stir bar, was charged with 52 mg (0.06 mmol) of $C_6F_5I(NTf_2)_2$ in a glove box. To the reactor was added approximately 600 mg (about 2.13 mmol) of $HNTf_2$ and 9 μL (0.1 mmol) of dry benzene was added. The reactor was heated to 120° C. with stirring at 1000 rpm for 30 minutes. The reactor was cooled to room temperature, the contents of the reactor were dissolved in approximately 0.5 mL HOTFA, and 0.1 mmol 1,1,2,2-TCE was added as an internal standard. The formation of products was determined by $^1H$ NMR of the reaction mixture using an acetone-$d_6$ coaxial for locking and shimming with the 1,1,2,2-TCE calibrated at 5.63 ppm.

The total yield of all products $PhNTf_2$ (7%) and the iodine adduct, $C_6F_5I(Ph)(NTf_2)$ (93%), based on $C_6F_5I(NTf_2)_2$ added, was 100% and can be seen in Table 1, entry 11.

Example 13

This example demonstrates the oxidation of ethane in the presence of oxidizing electrophile p-nitro-phenyl iodo $(NTf_2)_2$, generated in-situ from p-nitrophenylbis(trifluoroacetoxy)iodide.

Figure 9:
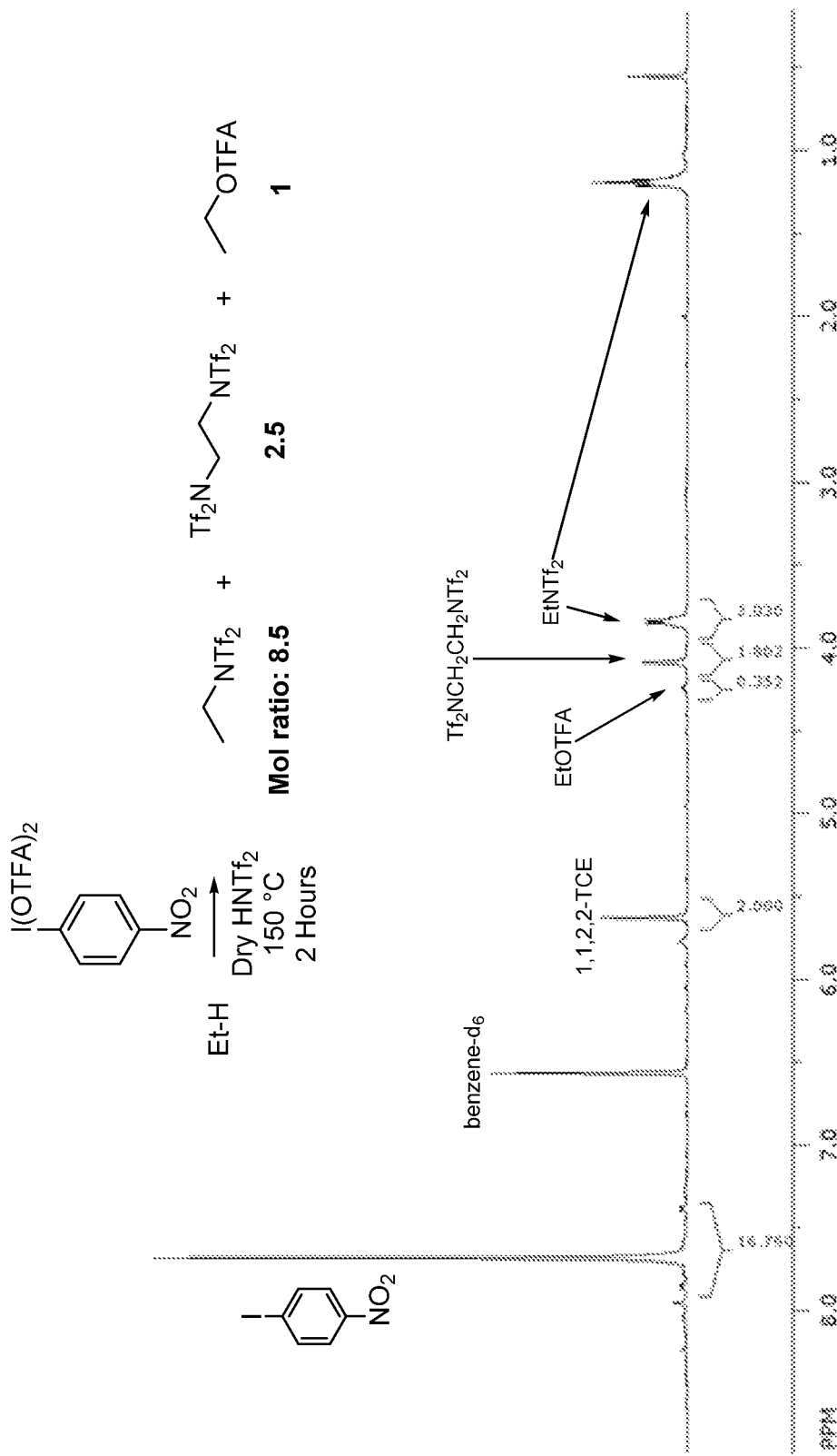
FIG. 9 illustrates the $^1$H NMR spectrum of the crude reaction mixture from the reaction of p-nitro-phenyl iodo (NTf$_2$)$_2$ with ethane in HNTf$_2$.

A small high pressure reactor containing a glass insert with a PTFE-coated, magnetic stir bar was charged with 20 mg (0.041 mmol) of p-nitrophenyl-bis(trifluoroacetoxy)iodide and 500 mg of dry $HNTf_2$. The reactor was sealed and pressure degassed with 500 psig of argon (5×) followed by five cycles with 500 psig of ethane. The reactor was pressurized to 500 psig with ethane and placed in an aluminum heating block at 150° C. for 3 hours. Post reaction, the reactor was cooled rapidly in a dry ice/acetone bath. It was then warmed back to room temperature, and the pressure was slowly released. The reactor was opened, and the solid contents were dissolved in 0.5 mL of HOTFA containing 0.01 mmol of 1,1,2,2-tetrachlroethane as an internal standard. Product formation was determined by $^1H$ NMR using a benzene-$d_6$ coaxial and employing 20 second pulse delays to ensure quantitative relaxation. See FIG. 9 for an exemplary $^1H$ NMR spectrum of the product mixture.

The products observed post reaction were $EtNTf_2$ (0.015 mmol), EtOTFA (0.00177 mmol) and 1,2-di[bis(trifluoromethanesulfonyl)imido]-ethane (0.00451 mmol) for an overall yield of 61% based on oxidant. The ratio of products ($EtNTf_2$:EtTFA:diamine) was 8.5:1:2.5; the results are summarized in Table 1, entry 10.

Example 14

This example demonstrates the oxidation of ethane in the presence of oxidizing electrophile $Sb(NTf_2)_5$, generated in-situ from $[Sb(OMe)_5]_2$.

Figure 10:
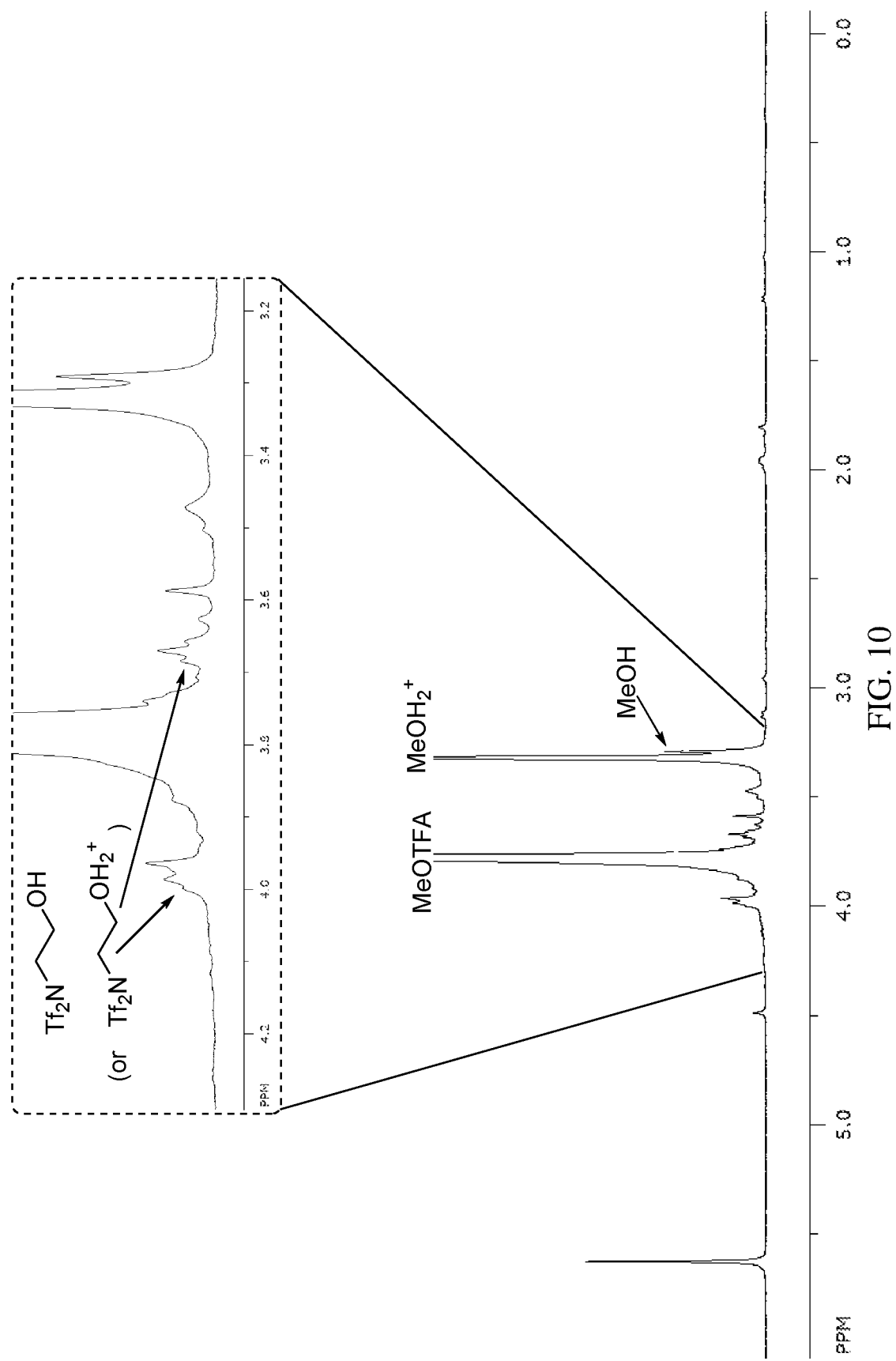
FIG. 10 illustrates the $^1$H NMR spectrum of the crude reaction mixture from the reaction of [Sb(OMe)$_5$]$_2$ with ethylene in HNTf$_2$.

A small high pressure reactor containing a glass insert with a PTFE-coated, magnetic stir bar was charged with 14 mg (0.025 mmol) of $[Sb(OMe)_5]_2$ and 500 mg of dry $HNTf_2$. The vial was hand tightened under argon and quickly sealed. With the inlet valve of the vial open, it was pressure degassed with argon, 5 times at 500 psig (about 35 kg/cm²). The vial was subsequently charged with 200 psig (about 7 kg/cm²) of a lecture bottle containing 8 psig of ethylene and 492 psig of argon, and the inlet valve was shut. The reactor was heated to 70° C. with stirring at 1000 rpm for 1 hour. The reactor was cooled to room temperature, and the pressure was slowly released. The contents of the vial insert were dissolved in approximately 0.5 mL HOTFA, and 0.1 mmol 1,1,2,2-TCE was added as an internal standard. The formation of products was determined by $^1H$ NMR of the reaction mixture using a benzene-$d_6$ coaxial for locking and shimming with the 1,1,2,2-TCE calibrated at 5.63 ppm. See FIG. 10 for an exemplary $^1H$ NMR spectrum of the product mixture.

The product observed post reaction was the mixed O—N functionalized product, $TFAO—CH_2CH_2NTf_2$ (0.0034 mmol) for an overall yield of 7% based on oxidant. The ethylene consumption based on the ideal gas law is ~10% of the reactor volume. The results are summarized in Table 1, entry 14.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for converting a hydrocarbon comprising at least one C—H bond to a nitrogen-functionalized product, comprising
contacting the hydrocarbon and
(i) an oxidizing electrophile comprising
(a) a main group element selected from the group consisting of arsenic, selenium, indium, tin, antimony, tellurium, thallium, lead, and bismuth in oxidized form and (b) at least one nitrogen-containing ligand of the formula —$NH_nY_{2-n}$, wherein Y is deactivated aryl, —F, —COR, —C(O)OR, —C(O)NRR', —$NO_2$, —NO, —$CH_2SO_2$, —$SO_2R$, —$SO_2F$, —$SO_2OH$, —$SO_2NH_2$, or P(O)RR', wherein R and R' are the same or different and each is aliphatic, heteroaliphatic, aromatic, or heteroaromatic, wherein the deactivated aryl comprises at least one electron withdrawing substituent selected from —$NO_2$, fluoro-$C_{1-8}$ alkyl, —F, —OOCR", —COOH, —$OH_2^+$, —$CONH_2$, —COOR", —$NR"_3^+$, —CN, —$SO_3H$, —$SO_3R"$, —$SO_3W$, and a combination thereof, wherein R" is hydrogen or an aliphatic, heteroaliphatic, aromatic, or heteroaromatic moiety, each of which is optionally substituted, W is a cation comprising a metal selected from boron, bismuth, antimony, arsenic, lanthanum, cerium, scandium, yttrium, titanium, zirconium, hafnium, silver, zinc, cadmium, aluminum, gallium, indium, germanium, tin, phosphorus, an alkali metal, and an alkaline earth metal, and n is 0 or 1, or (ii) an oxidant and a reduced form of an oxidizing electrophile comprising (a) a main group element selected from the group consisting of arsenic, selenium, indium, tin, antimony, tellurium, thallium, lead, and bismuth and (b) at least one nitrogen-containing ligand of the formula —$NH_nY_{2-n}$, wherein Y is deactivated aryl, —F, —COR, —C(O)OR, —C(O)NRR', —$NO_2$, —NO, —$CH_2SO_2$, —$SO_2R$, —$SO_2F$, —$SO_2OH$, —$SO_2NH_2$, or —P(O)RR', wherein R and R' are the same or different and each is aliphatic, heteroaliphatic, aromatic, or heteroaromatic, wherein the deactivated aryl comprises at least one electron withdrawing substituent selected from —$NO_2$, fluoro-$C_{1-8}$ alkyl, —F, —OOCR", —COOH, —$OH_2^+$, —$CONH_2$, —COOR", —$NR"_3^+$, —CN, —$SO_3H$, —$SO_3R"$, —$SO_3W$, and a combination thereof, wherein R" is hydrogen or an aliphatic, heteroaliphatic, aromatic, or heteroaromatic moiety, each of which is optionally substituted, and W is a cation comprising a metal selected from boron, bismuth, antimony, arsenic, lanthanum, cerium, scandium, yttrium, titanium, zirconium, hafnium, silver, zinc, cadmium, aluminum, gallium, indium, germanium, tin, phosphorus, an alkali metal, and an alkaline earth metal, and n is 0 or 1, in a solvent to provide the nitrogen-functionalized product and an electrophile reduction product; and optionally separating the nitrogen-functionalized product and the electrophile reduction product, wherein the hydrocarbon is selected from alkane, alkene, alkyne, cycloalkane, cycloalkene, heterocycloalkane, heterocycloalkene, arene, and heteroarene, each of which is optionally substituted, the hydrogen in the at least one C—H bond has been replaced with —$NH_nY_{2-n}$ from the at least one nitrogen-containing ligand, and the process does not contain an added halide ion.

2. The process of claim 1, comprising separating the nitrogen-functionalized product and the electrophile reduction product.

3. The process of claim 1, further comprising contacting the nitrogen-functionalized product with a compound of the formula H—Nu, which is a neutral or charged species, to form an $NH_2$-containing compound, wherein Nu is a nucleophilic group that enables the formation of the $NH_2$-containing compound.

4. The process of claim 3, wherein Nu comprises oxide, hydroxide, alkoxide, aryloxide, carboxylate, thiolate, bisulfide, optionally protected amide, or optionally protected azanide.

5. The process of claim 3, wherein Nu is —O, —$OR^1$, —$CO_2R^1$, —S, —$SR^1$, —$NR^1$, —$NHR^1$, or —$NR^1R^2$, in which $R^1$ and $R^2$ are the same or different and each is hydrogen, aliphatic, heteroaliphatic, aromatic, or heteroaromatic.

6. The process of claim 3, wherein the $NH_2$-containing compound comprises a monoamine, a diamine, or both a monoamine, and a diamine.

7. The process of claim 1, further comprising contacting the electrophile reduction product and an oxidizing regeneration reagent to regenerate the oxidizing electrophile.

8. The process of claim 1, wherein the hydrocarbon is selected from alkane, cycloalkane, and arene, each of which is optionally substituted.

9. The process of claim 1, wherein the oxidizing electrophile comprises the element thallium, lead, antimony, selenium, tellurium, or bismuth.

10. The process of claim 1, wherein Y is deactivated aryl, —F, —$NO_2$, —NO, —$CH_2SO_2$, —$SO_2F$, —$SO_2OH$, —$SO_2NH_2$, or —P(O)RR', wherein R and R' are the same or different and each is aliphatic, heteroaliphatic, aromatic, or heteroaromatic, wherein the deactivated aryl comprises at least one electron withdrawing substituent selected from —$NO_2$, fluoro-$C_{1-8}$ alkyl, —F, —OOCR", —COOH, —$OH_2^+$, —$CONH_2$, —COOR", —$NR"_3^+$, —CN, —$SO_3H$, —$SO_3R"$, —$SO_3W$, and a combination thereof, wherein R" is hydrogen or an aliphatic, heteroaliphatic, aromatic, or heteroaromatic moiety, each of which is optionally substituted, and W is a cation comprising a metal selected from boron, bismuth, antimony, arsenic, lanthanum, cerium, scandium, yttrium, titanium, zirconium, hafnium, silver, zinc, cadmium, aluminum, gallium, indium, germanium, tin, phosphorus, an alkali metal, and an alkaline earth metal.

11. The process of claim 1, wherein Y is —COR, —C(O)OR, —C(O)NRR', or —$SO_2R$, wherein R and R' are the same or different and each is aliphatic, heteroaliphatic, aromatic, or heteroaromatic.

12. The process of claim 1, wherein the oxidizing electrophile is of the formula $M^m(NH_nY_{2-n})_pL_q$, wherein M is a cation of the main group element, Y is deactivated aryl, —F, —COR, —C(O)OR, —C(O)NRR', —$NO_2$, —NO, —$CH_2SO_2$, —$SO_2R$, —$SO_2F$, —$SO_2OH$, —$SO_2NH_2$, or —P(O)RR', wherein R and R' are the same or different and each is aliphatic, heteroaliphatic, aromatic, or heteroaromatic, wherein the deactivated aryl comprises at least one electron withdrawing substituent selected from —$NO_2$, fluoro-$C_{1-8}$ alkyl, —F, —OOCR", —COOH, —$OH_2^+$, —$CONH_2$, —COOR", —$NR"_3^+$, —CN, —$SO_3H$, —$SO_3R"$, —$SO_3W$, and a combination thereof, wherein R" is hydrogen or an aliphatic, heteroaliphatic, aromatic, or heteroaromatic moiety, each of which is optionally substituted, and W is a cation comprising a metal selected from boron, bismuth, antimony, arsenic, lanthanum, cerium, scandium, yttrium, titanium, zirconium, hafnium, silver, zinc, cadmium, aluminum, gallium, indium, germanium, tin, phosphorus, an alkali metal, and an alkaline earth metal, L is a ligand, m is the formal oxidation state of M, n is 0 or 1, p is 1 to m, and q is 0 to 5.

13. The process of claim 12, wherein m is 1-8.

14. The process of claim 1, wherein the solvent is a non-oxidizable liquid selected from a fluorinated hydrocarbon, a sulfone, a deactivated arene, a deactivated aliphatic, a deactivated heteroarene, a deactivated heteroaliphatic, a compound of the formula $HNY_2$ or $H_2NY$, and any combination thereof, wherein Y is aryl, —F, —COR, —C(O)OR, —C(O)NRR', —$NO_2$, —NO, —$CH_2SO_2$, —$SO_2R$, —$SO_2F$, —$SO_2OH$, —$SO_2NH_2$, or —P(O)RR', and R and R' are the same or different and each is aliphatic, heteroaliphatic, aromatic, or heteroaromatic.

* * * * *